US008357542B2

(12) United States Patent
Kimoto et al.

(10) Patent No.: US 8,357,542 B2
(45) Date of Patent: Jan. 22, 2013

(54) SUSPENDED PARTICULATE MATTER MEASUREMENT APPARATUS AND SUSPENDED PARTICULATE MATTER MEASUREMENT METHOD USING THE SAME

(75) Inventors: Takashi Kimoto, Osaka (JP); Yoichi Mitani, Osaka (JP); Xiang Gao, Osaka (JP); Akiko Fukunaga, Osaka (JP); Saori Kitayama, Osaka (JP)

(73) Assignee: Kimoto Electric Co., Ltd., Osaka (JP)

( * ) Notice: Subject to any disclaimer, the term of this patent is extended or adjusted under 35 U.S.C. 154(b) by 125 days.

(21) Appl. No.: 12/764,988

(22) Filed: Apr. 22, 2010

(65) Prior Publication Data

US 2010/0330690 A1 Dec. 30, 2010

(30) Foreign Application Priority Data

Jun. 30, 2009 (JP) ................................. 2009-156392

(51) Int. Cl.
  *G01N 31/00* (2006.01)
  *G01N 23/06* (2006.01)
  *G01N 23/02* (2006.01)
  *G01N 23/00* (2006.01)

(52) U.S. Cl. ....... 436/163; 250/288; 250/281; 73/28.04; 73/28.01; 73/23.2; 73/23.37; 73/23.35

(58) Field of Classification Search .................. 436/163; 250/288, 281; 73/28.04, 28.01, 23.2, 23.37, 73/23.35
See application file for complete search history.

(56) References Cited

U.S. PATENT DOCUMENTS

| 4,401,763 | A | * | 8/1983 | Itoh | ................................. | 436/115 |
| 6,187,596 | B1 | * | 2/2001 | Dallas et al. | .................. | 436/169 |
| 6,865,926 | B2 | * | 3/2005 | O'Brien et al. | .............. | 73/23.27 |
| 2003/0082918 | A1 | * | 5/2003 | Hayasaka et al. | ............. | 438/706 |
| 2005/0145108 | A1 | * | 7/2005 | Rubin et al. | ..................... | 95/226 |
| 2008/0050833 | A1 | * | 2/2008 | Smith et al. | ..................... | 436/86 |

FOREIGN PATENT DOCUMENTS

JP 3574045 A 7/2004

OTHER PUBLICATIONS

English Translation of JP 3574045 (submitted on IDS on Apr. 22, 2010) obtained on Aug. 26, 2010.*
Douglas W. Dockery et al., "An Association between Air Pollution and Mortality in Six U.S. Cities," The New England Journal of Medicine, Dec. 9, 1993, pp. 1753-1759, vol. 329, Massachusetts Medical Society, MA.

* cited by examiner

*Primary Examiner* — Christine T Mui
(74) *Attorney, Agent, or Firm* — Judge Patent Associates

(57) ABSTRACT

Provided are a suspended particulate matter measurement apparatus capable of automatically measuring a nitrate ion content and a sulfate ion content in the atmosphere, and a suspended particulate matter measurement method using the same. The suspended particulate matter measurement apparatus includes a filter, suction part, extraction part, measurement part, and a recording part. The suction part suctions air in the atmosphere at a constant flow rate to cause particulate matter contained therein to be adsorbed onto the filter. The extraction part extracts components of the particulate matter adsorbed onto the filter, by dissolving the particulate matter into a solvent, and collects a resultant solution. The measurement part measures at least one of a nitrate ion content and a sulfate ion content in the solution collected by the extraction part, and outputs the measurement result. The recording part records the measurement result outputted from the measurement part.

13 Claims, 18 Drawing Sheets

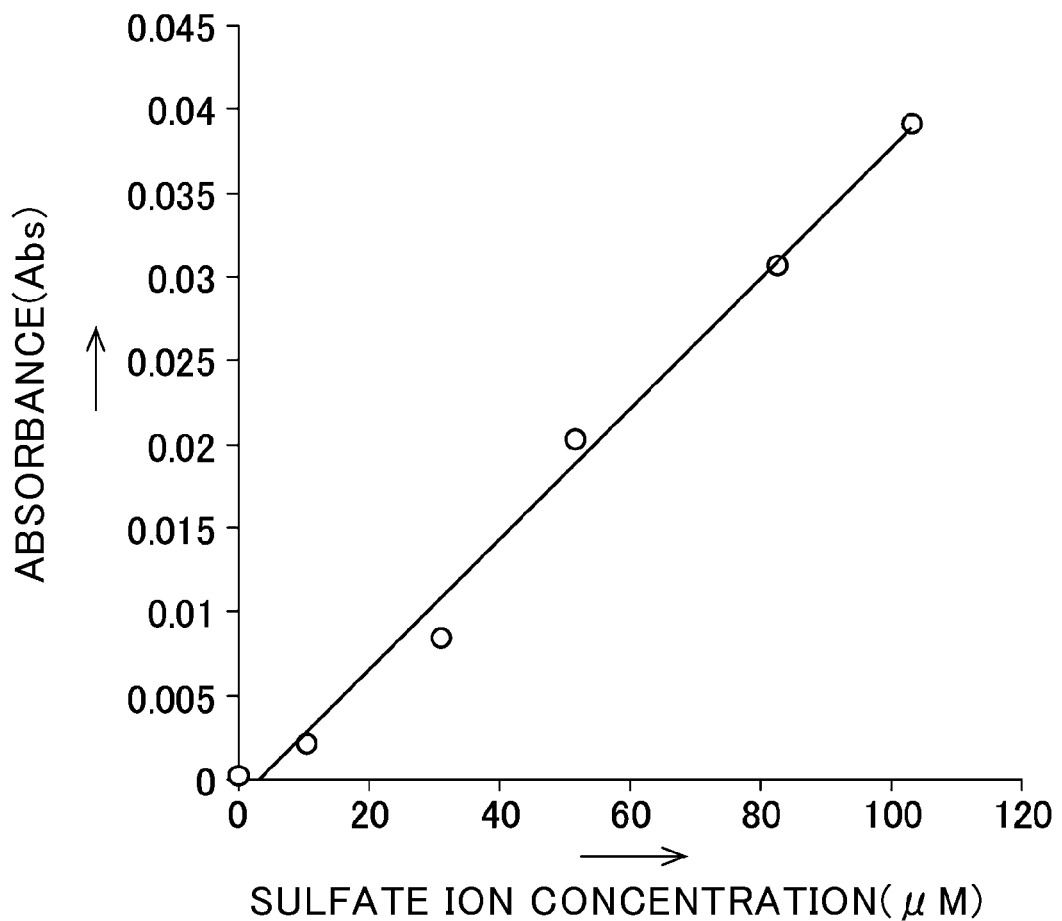
F I G. 1 3

F I G. 1 9
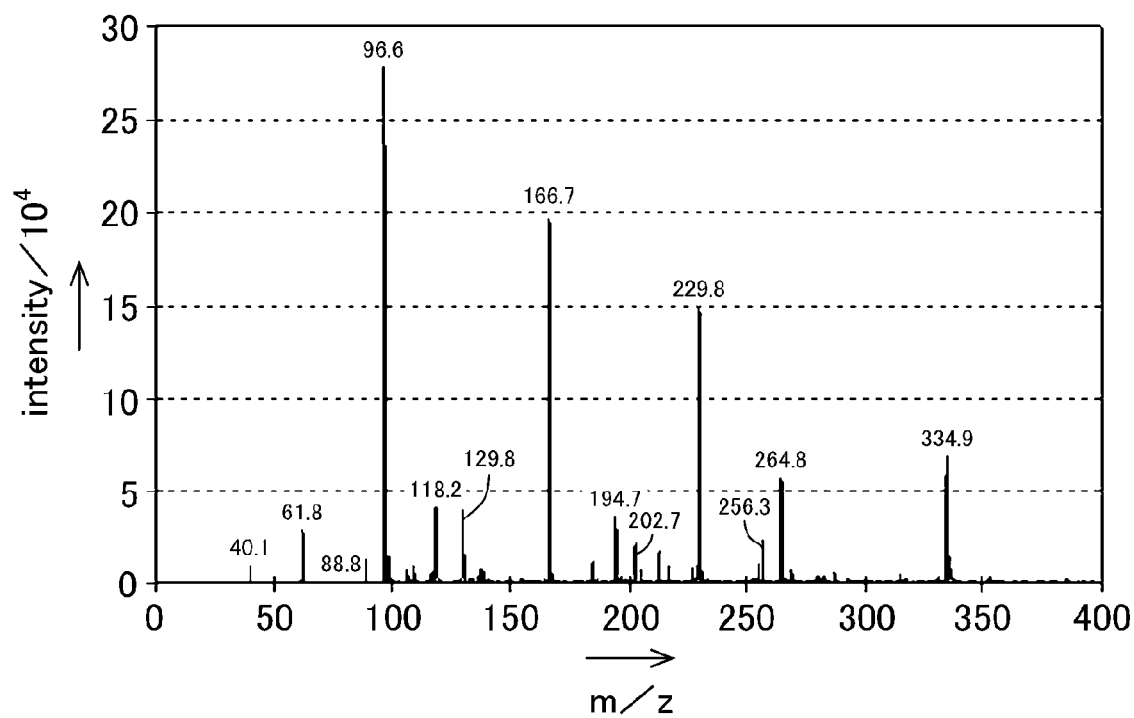

SUSPENDED PARTICULATE MATTER MEASUREMENT APPARATUS AND SUSPENDED PARTICULATE MATTER MEASUREMENT METHOD USING THE SAME

BACKGROUND OF THE INVENTION

1. Field of the Invention

The present invention relates to a suspended particulate matter measurement apparatus for collecting suspended particulate matter in the atmosphere and measuring the components of the collected particulate matter, and also relates to a suspended particulate matter measurement method that uses the suspended particulate matter measurement apparatus to measure the particulate matter.

2. Description of the Background Art

The recent studies indicate that sulfate ion is one of the main components of suspended particulate matter in the atmosphere. Epidemiologically, nitrate ion, sulfate ion, and acidity of suspended particulate matter are considered to be factors determining the toxicity of the suspended particulate matter (see, e.g., D. W. Dockery, et al., N. Engl. J. Med., 329, 1753-1759 (1993); hereinafter referred to as Non-Patent document 1).

As a suspended particulate matter measurement apparatus of conventional art, the applicant of the present invention has proposed a suspended particulate matter measurement apparatus for classifying and measuring total suspended particulate matter and fine suspended particulate matter (see, e.g., Japanese Patent No. 3574045; hereinafter refereed to as Patent Document 1). The conventional suspended particulate matter measurement apparatus is configured to include: a classification apparatus for classifying suspended particulate matter into coarse suspended particulate matter and fine suspended particulate matter; and calculating/recording means for calculating and automatically recording the amount of total suspended particulate matter and the amount of fine suspended particulate matter.

The suspended particulate matter measurement apparatus of the conventional art is capable of measuring the amount of total suspended particulate matter, the amount of fine suspended particulate matter, the amount of nitrate ion, and the amount of sulfate ion, which are contained in the atmosphere. However, the conventional suspended particulate matter measurement apparatus cannot automatically measure the amount of nitrate ion and sulfate ion contained in the atmosphere.

SUMMARY OF THE INVENTION

An object of the present invention is to provide a suspended particulate matter measurement apparatus capable of automatically measuring the amount of nitrate ion and sulfate ion contained in the atmosphere, and to provide a suspended particulate matter measurement method using the suspended particulate matter measurement apparatus.

The suspended particulate matter measurement apparatus according to the present invention is configured to include: a filter, a suction part, an extraction part, a measurement part, and a recording part. The filter collects particulate matter contained in the atmosphere. The suction part suctions air in the atmosphere at a constant flow rate to cause the particulate matter contained in the atmosphere to be collected by the filter. The extraction part extracts a component of the particulate matter collected by the filter, by dissolving the particulate matter into a solvent, and collects a resultant solution. The measurement part measures at least one of an amount of nitrate ion and an amount of sulfate ion that are contained in the solution collected by the extraction part, and outputs a measurement result. The recording part records the measurement result outputted from the measurement part.

According to the present invention, the measurement part further measures an amount of water-soluble organic matter contained in the solution, and outputs a measurement result; and the recording part further records the measurement result of the amount of water-soluble organic matter, the measurement result being outputted from the measurement part.

Still further, according to the present invention, the measurement part further measures a pH of the solution and thereby measures an acidity of the particulate matter contained in the atmosphere; and the recording part further records a measurement result of the acidity, the measurement result being outputted from the measurement part.

Still further, according to the present invention, the filter is formed as a tape-like filter, and the suspended particulate matter measurement apparatus is configured to further include a filter feeder. The filter feeder continuously feeds the tape-like filter.

Still further, according to the present invention, the suspended particulate matter measurement apparatus is configured to further include a classification part. The classification part classifies the particulate matter contained in the air suctioned by the suction part, by separating the air suctioned by the suction part into first air and second air. The first air contains particles of which a particle diameter is greater than 2.5 µm and of which a mass proportion in the first air is large. The second air contains particles of which a particle diameter is equal to or less than 2.5 µm and of which a mass proportion in the second air is large. The particulate matter having been classified by the classification part is collected at a plurality of different positions on the filter.

Still further, according to the present invention, the measurement part includes a beta ray emitter and a beta ray receiving/measuring section. The beta ray emitter emits a beta ray to a position, on the filter, at which the particulate matter is collected. The beta ray receiving/measuring section receives the beta ray that is emitted by the beta ray emitter and transmitted through the filter, and measures an amount of the beta ray. The measurement part measures, by a beta ray absorption method, a mass of the particulate matter collected by the filter.

Still further, according to the present invention, the measurement part measures the amount of nitrate ion by an absorbance method with which to measure an absorbance of the solution at a predetermined wavelength.

Still further, according to the present invention, the measurement part measures the amount of sulfate ion by barium sulfate turbidimetry.

Still further, according to the present invention, the measurement part measures, after a pH indicator being added to the solution, the acidity of the particulate matter based on the pH of the solution by an absorbance method with which to measure an absorbance of the solution at a particular wavelength.

Still further, according to the present invention, the measurement part measures the amount of water-soluble organic matter by an absorbance method with which to measure an absorbance of the solution at a predetermined wavelength.

Still further, according to the present invention, the measurement part performs the measurement by either ion chromatography or mass spectrometry.

Still further, according to the present invention, the measurement part performs the measurement by mass spectrometry, and includes a quadrupole mass spectrometer.

Still further, according to the present invention, the measurement part performs the measurement by mass spectrometry and performs ionization by electrospray ionization.

Still further, according to the present invention, the measurement part performs the measurement by ion chromatography, and the measurement part includes at least one of a cation measurement part for detecting a positive ion and performing ion chromatography and an anion measurement part for detecting a negative ion and performing ion chromatography.

The suspended particulate matter measurement method according to the present invention uses a suspended particulate matter measurement apparatus. The suspended particulate matter measurement apparatus includes a filter, a suction part, an extraction part, a measurement part, and a recording part. The filter collects particulate matter contained in the atmosphere. The suction part suctions air in the atmosphere at a constant flow rate to cause the particulate matter contained in the atmosphere to be collected by the filter. The extraction part extracts a component of the particulate matter collected by the filter, by dissolving the particulate matter into a solvent, and collects a resultant solution. The measurement part measures an amount of nitrate ion and an amount of sulfate ion that are contained in the solution collected by the extraction part, and measures an acidity of the solution, and outputs measurement results. The recording part records the measurement results outputted from the measurement part.

The suspended particulate matter measurement method includes a nitrate ion measurement process, an acidity measurement process, and a sulfate ion measurement process. In the nitrate ion measurement process, the amount of nitrate ion is measured by an absorbance method with which to measure an absorbance of the solution at a predetermined wavelength. In the acidity measurement process performed subsequent to the nitrate ion measurement process, a pH indicator is added to the solution, and then a pH of the solution is measured by an absorbance method with which to measure an absorbance of the solution at a particular wavelength, whereby an acidity of the particulate matter is measured. In a sulfate ion measurement process performed subsequent to the acidity measurement process, the amount of sulfate ion is measured by barium sulfate turbidimetry.

According to the present invention, the suction part suctions air in the atmosphere at a constant flow rate so as to cause particulate matter contained in the atmosphere to be collected by the filter. The extraction part extracts the components of the particulate matter collected by the filter, by dissolving the particulate matter into a solvent, and collects a resultant solution. The measurement part measures at least one of the amount of nitrate ion and the amount of sulfate ion that are contained in the solution collected by the extraction part, and outputs the measurement results. In this manner, the components of particulate matter contained in a substantial amount of air in the atmosphere can be condensed into a small amount of solution and then collected. Accordingly, at least one of the amount of nitrate ion and the amount of sulfate ion, which are contained in particulate matter in the atmosphere, can be automatically measured with high sensitivity.

In the conventional technique, the measurement is performed after the collection of particulate matter, which involves manual work, has been performed for 24 hours. However, the present invention can perform the measurement after the collection has been performed for approximately one hour. This reduces a time period during which the collected particulate matter is exposed to the flow of air, thereby preventing chemical alteration of the particulate matter. If collection of acid particulate matter is performed for a long period of time, the acid particulate matter is neutralized by gaseous ammonia. Therefore, accurate measurement of acid particulate matter cannot be performed with the conventional technique. However, the present invention, which requires only a short period of time for the collection, can perform accurate measurement of acid particulate matter. Moreover, some types of water-soluble organic matter contain volatile substances, and therefore, a loss of such volatile substances occurs if the collection is performed for 24 hours. However, the present invention allows the measurement to be performed while suppressing dispersion and volatilization of substances.

Accordingly, the present invention enables highly precise measurement. Since the recording part records measurement results, the recorded measurement results can be referenced after the measurement has been performed. This contributes to conducting an epidemiological investigation and an investigation into particulate matter emission sources, and to taking measures against air pollution.

According to the present invention, the measurement part further measures the amount of water-soluble organic matter contained in the solution, and outputs the measurement result. The recording part further records the measurement result of the amount of water-soluble organic matter, which measurement result is outputted from the measurement part. In this manner, the amount of water-soluble organic matter contained in particulate matter in the atmosphere can be measured.

Further, according to the present invention, the measurement part further measures the pH of the solution, thereby measuring the acidity of particulate matter contained in the atmosphere. The recording part further records the measurement result of the acidity, which is outputted from the measurement part. In this manner, temporal changes in the amount of acid substances contained in the atmosphere and an increase/decrease of effects on the environment caused thereby can be automatically measured. This contributes to conducting investigation into, and taking measures against, the effects of suspended particulate matter on the environment, such as acid rain.

Still further, according to the present invention, the filter is formed as a tape-like filter, and the suspended particulate matter measurement apparatus is configured to further include a filter feeder. The filter feeder continuously feeds the tape-like filter. Accordingly, at least one of the amount of nitrate ion and the amount of sulfate ion that are contained in particulate matter in the atmosphere can be continuously measured.

Still further, according to the present invention, the suction part causes particulate matter in which the mass proportion of particles whose diameter exceeds a predetermined particle diameter is large, and particulate matter in which the mass proportion of particles whose diameter is equal to or less than the predetermined particle diameter is large, to be collected at a plurality of different positions on the filter, respectively. This enables measurement of components of particulate matter that has such a particle diameter as to have particularly significant effects on the human body. There is a correlation between the particle diameter of particulate matter and the effects of the particulate matter on the human body. Since the suspended particulate matter measurement apparatus according to the present invention is capable of classifying particulate matter with reference to a predetermined particle diameter, the suspended particulate matter measurement apparatus can perform measurement with a focus on, among particulate matter of various particle diameters, particulate matter having such a particle diameter as to have significant effects on the human body, and measure at least one of the amount of nitrate ion and the amount of sulfate ion that are contained in such particulate matter.

Still further, according to the present invention, the measurement part measures the mass of the particulate matter collected by the filter, by using a beta ray absorption method. In this manner, the entire amount of particulate matter contained in a fixed amount of air in the atmosphere can be measured. Also, at least one of the amount of nitrate ion and the amount of sulfate ion that are contained in a fixed amount of particulate matter can be measured. Accordingly, the proportion of the amount of nitrate ion or sulfate ion in the entire particulate matter can be determined. This contributes to conducting an epidemiological investigation and an investigation into particulate matter emission sources, and to taking measures against air pollution.

In the measurement using a beta ray absorption method, the mass of the particulate matter collected by the filter can be measured without causing chemical alteration of the particulate matter. Also, the particulate matter collected by the filter is not consumed in the measurement of the mass. Therefore, the particulate matter collected by the filter can be entirely extracted using a solvent, and a resultant solution containing the components of the particulate matter can be collected. This prevents errors from occurring when measurement different from the mass measurement is performed on the particulate matter.

According to the present invention, the measurement part measures the amount of nitrate ion in the solution by an absorbance method with which to measure absorbances of the solution at predetermined wavelengths. Accordingly, even if the amount of nitrate ion contained in the solution is less than a scale of, for example, several tens of nanomole per cubic meter (several 10 s of $nmol/m^3$), the amount of nitrate ion can be measured with high precision. Moreover, the amount of nitrate ion can be measured within a shorter time period in a simpler and more convenient manner than in a case, for example, where the amount of nitrate ion is measured by manual sampling and ion chromatography. Furthermore, the amount of nitrate ion contained in the collected particulate matter can be measured within a shorter time period than a time period required for collecting the particulate matter.

Since the measurement can be completed within a short time period, even if the collection of particulate matter for the next measurement is performed in parallel with the measurement of particulate matter that has already been collected and extracted, the measurement of the particulate matter extracted next can be performed without having to wait for the end of the preceding measurement by the measurement part. Since the extraction and measurement of the collected particulate matter can be performed immediately after the collection, the possibility of systematic errors being contained in the measurement results due to a presence of a time period during which the collected particulate matter is left unmeasured until the preceding measurement by the measurement part is completed, can be minimized. Since the collection of particulate matter for the next measurement can be started immediately after the end of the preceding collection of particulate matter, the measurement of particulate matter contained in the atmosphere can be continuously performed.

According to the present invention, the measurement part measures the amount of sulfate ion in the solution by barium sulfate turbidimetry. Accordingly, even if the amount of sulfate ion contained in the solution is less than a scale of, for example, several tens of nanomole per cubic meter (several 10 s of $nmol/m^3$), the amount of sulfate ion can be measured with high precision. Moreover, the amount of sulfate ion can be measured within a shorter time period in a simpler and more convenient manner than in a case where, for example, the amount of sulfate ion is measured by manual sampling and ion chromatography. Furthermore, the amount of sulfate ion contained in the collected particulate matter can be measured within a shorter time period than a time period required for collecting the particulate matter.

Therefore, even if the collection of particulate matter for the next measurement is performed in parallel with the measurement of particulate matter that has already been collected and extracted, the measurement of the particulate matter extracted next can be performed without having to wait for the end of the preceding measurement by the measurement part. Since the extraction and measurement of the collected particulate matter can be performed immediately after the collection, the possibility of systematic errors being contained in the measurement results due to a presence of a time period during which the collected particulate matter is left unmeasured until the preceding measurement by the measurement part is completed, can be minimized. Since the collection of particulate matter for the next measurement can be started immediately after the end of the preceding collection of particulate matter, the measurement of particulate matter contained in the atmosphere can be continuously performed.

According to the present invention, the measurement part determines the acidity of the solution by measuring, after a pH indicator being added to the solution, the pH of the solution by using an absorbance method with which to measure absorbances of the solution at particular wavelengths. In this manner, the acidity of the solution that contains particulate matter can be measured by using the measurement part that measures at least one of nitrate ion and sulfate ion. Consequently, as compared to a case where, for example, acidity measurement is performed by manual sampling and a pH electrode, measurement can be performed with a suppressed occurrence of systematic errors that are due to neutralization caused by gaseous ammonia during the sampling.

Further, according to the present invention, the measurement part measures the amount of water-soluble organic matter in the solution by an absorbance method with which to measure an absorbance of the solution at a predetermined wavelength. This allows the amount of water-soluble organic matter to be measured within a shorter time period than a time period required for collecting the particulate matter. Accordingly, even if the collection of particulate matter for the next measurement is performed in parallel with the extraction and measurement of particulate matter that has already been collected, the measurement of the particulate matter collected next can be performed without having to wait for the end of the preceding measurement by the measurement part. Since the extraction and measurement of the collected particulate matter can be performed immediately after the collection, the possibility of systematic errors being contained in the measurement results due to a presence of a time period during which the collected particulate matter is left unmeasured until the preceding measurement by the measurement part is completed, can be minimized. Since the collection of particulate matter for the next measurement can be started immediately after the end of the preceding collection of particulate matter, the measurement of particulate matter contained in the atmosphere can be continuously performed.

Still further, according to the present invention, the measurement part performs measurement by either ion chromatography or mass spectrometry. In this manner, easily ionized substances that are contained in suspended particulate matter can be measured. Easily ionized substances are often associated with the acidity of suspended particulate matter. Therefore, by measuring such substances, information that contributes to identifying substances associated with the acidity can be obtained.

Still further, according to the present invention, the measurement part performs measurement by mass spectrometry, and includes a quadrupole mass spectrometer. As a result, the measurement can be completed within a shorter time period than in a case where, for example, a time of flight (abbreviated as "TOF") mass spectrometer is used. Since the measurement can be completed within a short time period, even if the collection of particulate matter for the next measurement is performed in parallel with the measurement of particulate matter that has already been collected and extracted, the measurement of the particulate matter extracted next can be performed without having to wait for the end of the preceding measurement by the measurement part.

Since the extraction and measurement of the collected particulate matter can be performed immediately after the collection, the possibility of systematic errors being contained in the measurement results due to a presence of a time period during which the collected particulate matter is left unmeasured until the preceding measurement by the measurement part is completed, can be minimized. Since the collection of particulate matter for the next measurement can be started immediately after the end of the preceding collection of particulate matter, the measurement of particulate matter contained in the atmosphere can be continuously performed.

Still further, according to the present invention, the measurement part performs ionization using electrospray ionization. Electrospray ionization allows energy applied to molecules to be lower than other various ionization methods such as fast atom bombardment and electron ionization. Therefore, there is less chance of a chemical bond between molecules being broken, and molecular fragmentation can be suppressed, accordingly. This allows a parent peak to be readily specified.

Still further, according to the present invention, the measurement part including at least one of the cation measurement part and the anion measurement part performs ion chromatography. Therefore, unlike cases where other types of chromatography are performed, molecules are not adsorbed onto the columns or samples to be measured are not required to have high volatility, for example. Accordingly, various ions contained in particulate matter can be measured.

Still further, according to the present invention, the amount of nitrate ion in the solution is measured in the nitrate ion measurement process by using an absorbance method with which to measure absorbances of the solution at predetermined wavelengths. In the acidity measurement process performed after the nitrate ion measurement process, a pH indicator is added to the solution, and the acidity of the particulate matter is determined by measuring the pH of the solution by an absorbance method with which to measure absorbances of the solution at particular wavelengths. In the sulfate ion measurement process performed after the acidity measurement process, the amount of sulfate ion is measured by barium sulfate turbidimetry.

Consequently, in the nitrate ion measurement process, the measurement can be performed without adding a reagent to the solution that has been collected by the extraction part. Since the pH indicator is added in the acidity measurement process, the measurement can be performed in the acidity measurement process even after the nitrate ion measurement process. Since added barium chloride and sulfate ion are suspended in the solution in the sulfate ion measurement process, the measurement can be performed in the sulfate ion measurement process even after the acidity measurement process. Thus, at least these three types of measurements can be performed using the same solution. Further, since the nitrate ion measurement process, the acidity measurement process, and the sulfate ion measurement process can use a common UV-Vis spectrometer, the measurement apparatus can be simplified than in a case where different measurement apparatuses are used for the respective measurement processes.

These and other objects, features, aspects and advantages of the present invention will become more apparent from the following detailed description of the present invention when taken in conjunction with the accompanying drawings.

BRIEF DESCRIPTION OF THE DRAWINGS

FIG. 13 shows a calibration curve that is obtained based on the data shown in FIG. 12;

FIG. 19 shows an example of measurement results obtained by a mass spectrometer 144 according to the third embodiment of the present invention.

DESCRIPTION OF THE PREFERRED EMBODIMENTS

Figure 1:
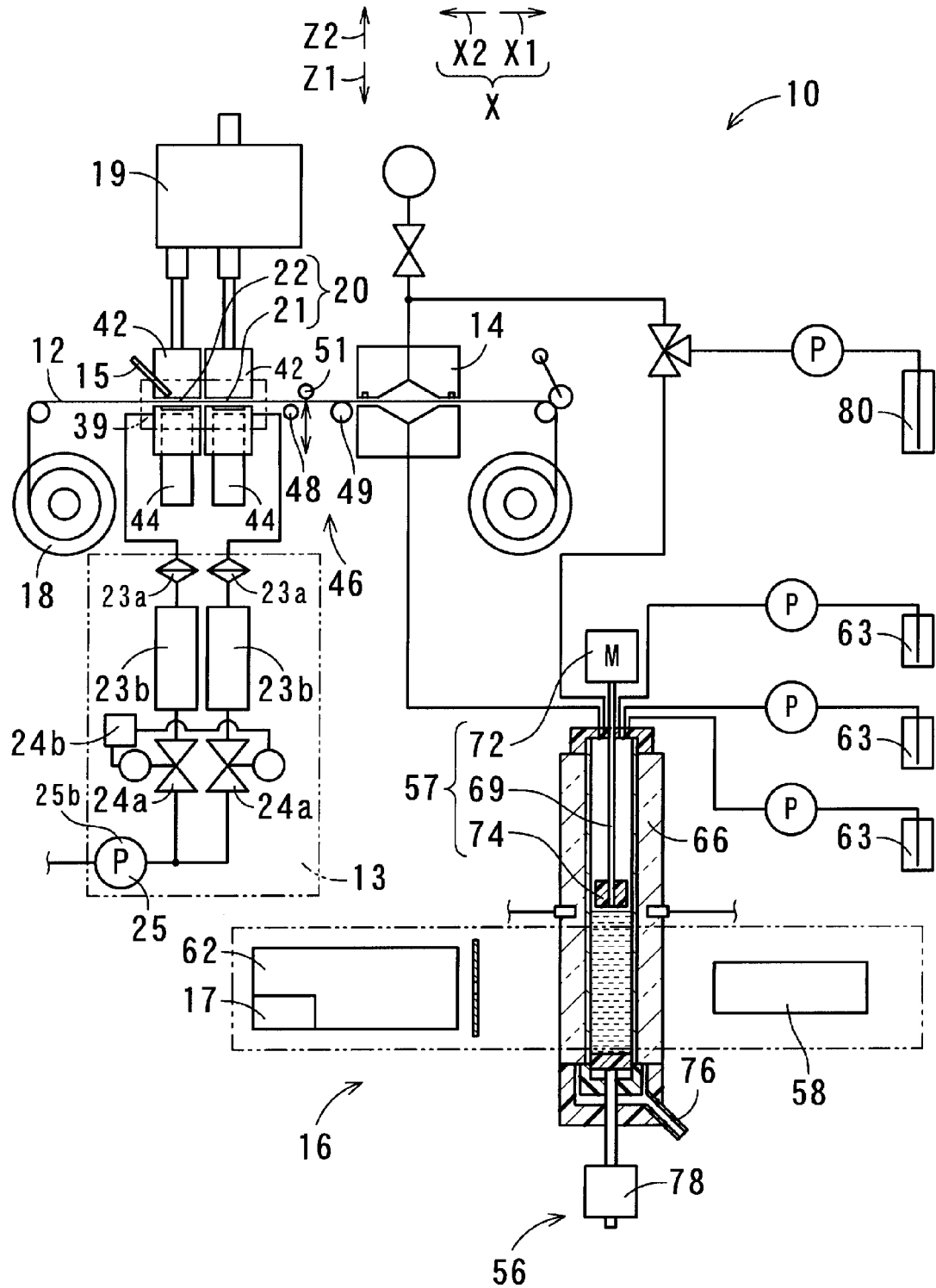
FIG. 1 shows a structure of a suspended particulate matter measurement apparatus 10 according to a first embodiment of the present invention.

Hereinafter, a plurality of embodiments of the present invention will be described with reference to the accompanying drawings. In the description of each embodiment below, matters already described in a preceding embodiment are denoted by the same reference numerals as those used in the preceding embodiment, and the description of those matters may be omitted. In the case of describing only a part of a configuration, the other parts of the configuration are the same as those described in a preceding description. Not only are the components combined as described in detail in the respective embodiments, but also the embodiments may be partially combined if the combination can be realized without hindrance. Moreover, the embodiments merely show examples for embodying the techniques according to the present invention. The technical scope of the present invention is not limited to these embodiments. Numerous variations of the techniques according to the present invention can be devised without departing from the technical scope defined in the claims. The descriptions below include descriptions of a suspended particulate matter measurement apparatus 10 and a suspended particulate matter measurement method.

First Embodiment

FIG. 1 shows a structure of the suspended particulate matter measurement apparatus 10 according to a first embodiment of the present invention. The suspended particulate matter measurement apparatus 10 of the present embodiment collects suspended particulate matter in the atmosphere (particulate matter 11), and measures the collected particulate matter 11. Similarly, the suspended particulate matter measurement method is for collecting suspended particulate matter in the atmosphere, and measuring the collected particulate matter 11. The suspended particulate matter measurement method is performed by using the suspended particulate matter measurement apparatus 10.

The suspended particulate matter measurement apparatus 10 is configured to include a filter 12, a suction part 13, an extraction part 14, a measurement part 16, and a recording part 17. The filter 12 collects particulate matter 11 contained in the atmosphere. To be specific, particulate matter 11 suspended in the atmosphere, which is solid or liquid matter, is adsorbed onto the filter 12. The suction part 13 suctions air in the atmosphere at a constant flow rate, thereby causing particulate matter 11 contained in the atmosphere to be adsorbed onto the filter 12. At the extraction part 14, the particulate matter 11 adsorbed onto the filter 12 is dissolved in a solvent, and thereby components of the particulate matter 11 are extracted, and the resultant solution is collected. The measurement part 16 measures at least one of the amount of nitrate ion and the amount of sulfate ion that are contained in the solution collected at the extraction part 14, and outputs the measurement result. The recording part 17 records the measurement result outputted from the measurement part 16.

The suspended particulate matter measurement apparatus 10 is configured to further include a filter feeder 18 and a classification part 19. The filter 12 is formed in a tape-like shape from a flexible material of polytetrafluoroethylene, i.e., so-called Teflon (registered trademark). Teflon (registered trademark) has higher resistance to chemicals than other resins, and is not dissolved by such a solvent as acetonitrile or by organic substances contained in particulate matter. In another embodiment, the filter 12 may not necessarily be formed from Teflon (registered trademark). For example, the filter 12 may be formed from a fluorine membrane different from Teflon (registered trademark). The filter 12 is only required to have flexibility, be in a tape-like shape, and be formed from a resin having chemical resistance.

The filter feeder 18 continuously feeds the tape-like filter 12. The classification part 19 separates the air suctioned by the suction part 13 into first air and second air, thereby classifying the particulate matter 11 contained in the air suctioned by the suction part 13. The first air contains particles of which the particle diameter is greater than 2.5 μm and of which the mass proportion in the first air is large. The second air contains particles of which the particle diameter is equal to or less than 2.5 μm and of which the mass proportion in the second air is large. The particulate matter 11 having been classified by the classification part 19 is adsorbed onto a plurality of different positions on the filter 12.

When an area on the filter 12, at which the air in the atmosphere suctioned by the suction part 13 passes through the filter 12, is referred to as a "collection area" 20, the classification part 19 is located at the opposite side to the suction part 13 with respect to the collection area 20. In the present embodiment, the classification part 19 classifies particulate matter 11 suspended in the atmosphere into two classes. Accordingly, two collection areas 20 are formed so as to be arranged along a moving direction X along which the filter 12 moves. For example, in the case where the classification part 19 classifies particulate matter 11 suspended in the atmosphere into a larger number of classes, the collection areas 20 are formed such that the number of collection areas corresponds to said larger number of classes. In the present embodiment, the two collection areas 20 are referred to as a "first collection area" 21 and a "second collection area" 22.

The suction part 13 includes air filters 23a, flow sensors 23b, flow regulating valves 24a, a flow controller 24b, and a suction pump 25. Among these components, the number of flow controllers 24b and the number of suction pumps 25 provided for one suspended particulate matter measurement apparatus 10 are each one. Whereas, the number of air filters 23a, the number of flow sensors 23b, and the number of flow regulating valves 24a to be provided each correspond to the number of collection areas 20 which is determined based on the number of classes into which the classification part 19 performs classification. Accordingly, in the present embodiment, two air filters 23a, two flow sensors 23b, and two flow regulating valves 24a are provided. The air from the classification part 19, which has passed through flow path tubes and the first and second collection areas 21 and 22, further travels through the air filters 23a, the flow sensors 23b, and the flow regulating valves 24a, and then passes through flow path tubes connected to the suction pump 25. In this manner, the air travels from the filter 12 to the suction pump 25.

The air filters 23a remove solid or liquid substances contained in the air passing through the air filters 23a. Although solid or liquid substances contained in the passing air are collected by the filter 12, the air further passes through the air filters 23a and thereafter passes through the flow sensors 23b and the flow regulating valves 24a. In this manner, solid or liquid substances are removed twice, and thereby prevented from entering the flow sensors 23b and the flow regulating valves 24a.

The flow sensors 23b each measure the flow rate, per unit time, of the air passing through the corresponding flow path tube, and output the measurement result to the flow controller 24b. The flow regulating valves 24a are each configured to include an orifice that is formed so as to be able to vary the flow path resistance. The flow controller 24b performs control so as to adjust the flow path resistance determined by the orifice. The flow controller 24b is realized by a computer, for example. The flow controller 24b controls the flow regulating valves 24a in accordance with outputs from the flow sensors 23b, thereby adjusting the flow rate, per unit time, of the air passing through the flow path tubes to a predetermined constant flow rate. Alternatively, the flow controller 24b may be formed so as to be integrated with a computer that is described below.

The suction pump 25 is realized by, for example, a vacuum pump, and suctions the air present within the flow path tubes. Preferably, the suction pump 25 is realized by a pump which is capable of suctioning approximately 20 liters of air per minute, and of which variation in the suction pressure is small, and which is capable of suctioning air with a stable constant pressure.

Figure 2:
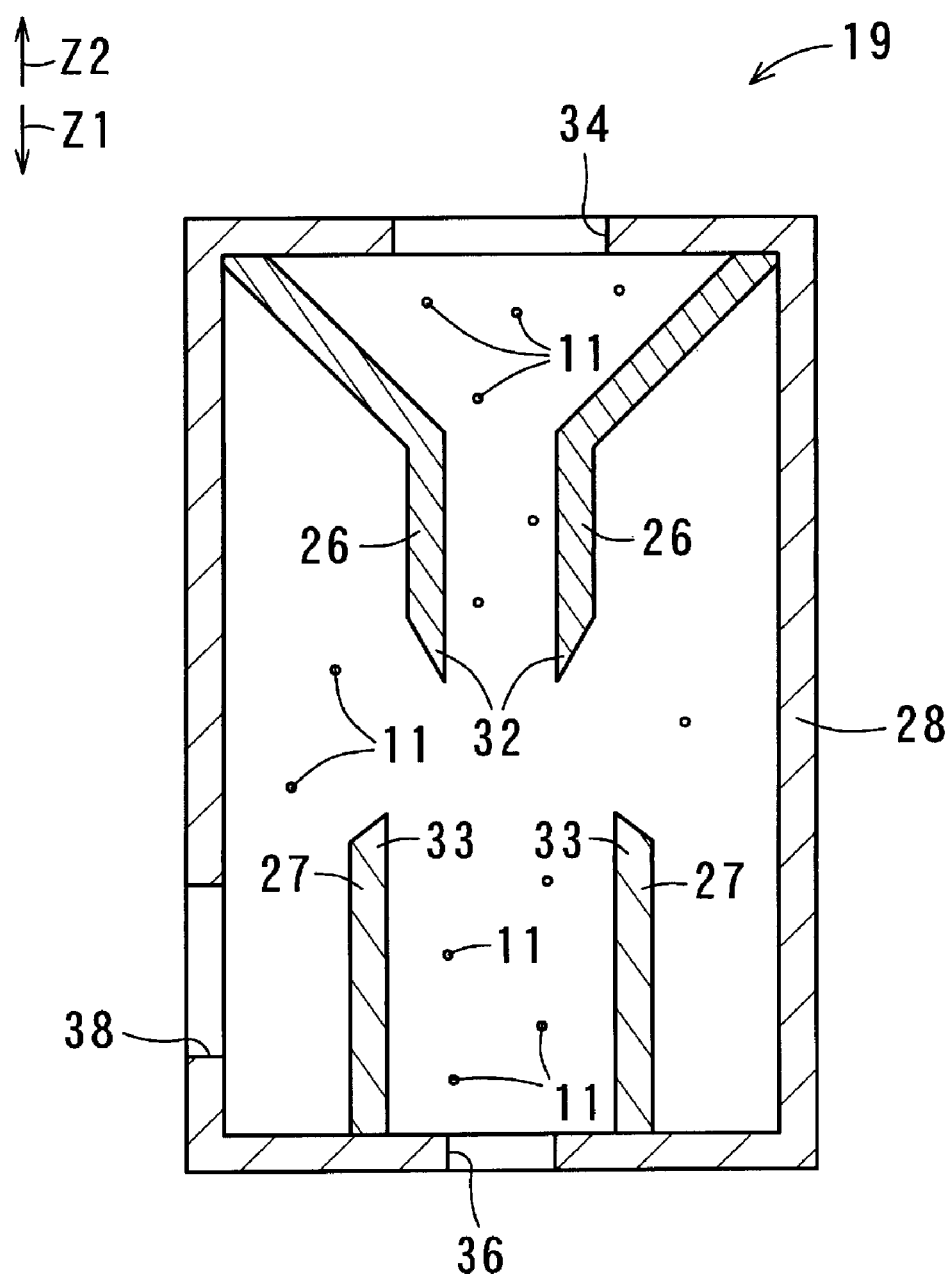
FIG. 2 is a cross-sectional view showing a classification part 19 of the first embodiment of the present invention.

FIG. 2 is a cross-sectional view showing the classification part 19 of the first embodiment of the present invention. To be specific, the classification part 19 is realized by a virtual impactor classifier. The virtual impactor classifier includes a nozzle 26, a partition wall 27, and an outer tube portion 28. The nozzle 26 is formed to have a tube-like shape such that the shorter the distance to the filter 12, the smaller is the inner diameter of the nozzle 26 through which the air in the atmosphere suctioned by the suction pump 25 travels toward the filter 12. The air having passed through an ejection opening end 32 of the nozzle 26, the ejection opening end 32 being formed at the filter 12 side of the nozzle 26, and suspended particulate matter dispersed in the air, travel toward the filter 12 with an initial velocity applied thereto. The nozzle 26 may be formed so as to have a portion of which the inner diameter is uniform, as long as the nozzle 26 has a portion of which the inner diameter is gradually reduced in accordance with a decrease in the distance to the filter 12.

The partition wall 27 is formed in a tubular shape having an axis aligned with an axis of the nozzle 26 that is also formed in a tubular shape. The partition wall 27 has an opening 33 at its tip that is the nearest portion of the partition wall 27 to the nozzle 26. The inner diameter of the opening 33 is set to be slightly greater than the inner diameter of the tip of the nozzle 26, which is the nearest portion of the nozzle 26 to the filter 12. The opening 33 is open toward the nozzle 26. A part of the air ejected per unit time through the ejection opening end 32 of the nozzle 26 enters the inside of the partition wall 27 through the opening 33. The ejection opening end 32 of the nozzle 26 and the opening 33 of the partition wall 27 are each formed to have a cylindrical shape.

The outer tube portion 28 is formed to have such a shape as to surround the nozzle 26 and the partition wall 27. Formed in the outer tube portion 28 are: an inlet 34 through which the air suctioned by the suction part 13 enters the outer tube portion 28; a partition wall outlet 36 through which the air having passed through the inside of the partition wall 27 exits; and an outer tube outlet 38 through which the air, which has entered and traveled through the nozzle 26 and passed outside the partition wall 27 and inside the outer tube portion 28, exits. The flow rate, per unit time, of the air suctioned by the suction part 13 is set to be constant. When, of the air ejected from the nozzle 26, the air entering the inside of the opening 33 of the partition wall 27 is referred to as the "first air", and the air traveling outside the opening 33 of the partition wall 27 is referred to as the "second air", the ratio between the flow rate of the first air per unit time and the flow rate of the second air per unit time is predetermined. For example, the ratio is set in accordance with the inner diameter of the nozzle 26 at the filter 12 side, i.e., the inner diameter of the ejection opening end 32, or the inner diameter of the opening 33 of the partition wall 27, or the distance between the ejection opening end 32 and the opening 33.

Particles contained in suspended particulate matter in the atmosphere are categorized by size, with reference to a particle diameter of approximately 2.5 µm, into coarse particles of which the particle diameter is greater than approximately 2.5 µm and fine particles of which the particle diameter is equal to or less than approximately 2.5 µm. When suspended particulate matter in the atmosphere is analyzed based on its particle diameter and the proportion of suspended particulate matter of each diameter is represented by a mass proportion, the mass proportion of particulate matter 11 having a particle diameter approximately 2.5 µm is less than the mass proportion of particulate matter 11 having a particle diameter greater than 2.5 µm and than the mass proportion of particulate matter 11 having a particle diameter smaller than 2.5 µm.

Of the air ejected from the nozzle 26, the air in which the mass proportion of coarse particles is large travels straight and enters the inside of the opening 33, and the air in which the mass proportion of fine particles is large travels outside the opening 33. Based on this, the particulate matter 11 having passed through the nozzle 26 is classified into the particulate matter 11 in which the mass proportion of coarse particles is large and the particulate matter 11 in which the mass proportion of fine particles is large. The particulate matter 11 in which the mass proportion of coarse particles is large and which is dispersed in the first air comes in contact with one of the two collection areas 20 on the filter 12, whereby the particulate matter 11 is collected. When, among the two collection areas 20, the area with which the first air comes in contact is referred to as the first collection area 21, the first air from which the dispersed particulate matter 11 has been removed passes through the first collection area 21. In the particulate matter 11 collected at the first collection area 21, the mass proportion of particles of which the particle diameter exceeds approximately 2.5 µm and is no greater than 10 µm, is large.

The particulate matter 11 in which the mass proportion of fine particles is large and which is dispersed in the second air comes in contact with the other one of the two collection areas 20, whereby the particulate matter 11 is collected. When the area with which the second air comes in contact is referred to as the second collection area 22, the second air from which the dispersed particulate matter 11 has been removed passes through the second collection area 22. The finer the particulate matter 11, the greater is the proportion of its surface area to its mass. Accordingly, the advancing direction of such finer particulate matter 11 has a greater tendency to vary due to a change in the advancing direction of the air. This allows the classification part 19 to classify the particulate matter 11.

In the present embodiment, the flow rate of the air passing through the filter 12 at the first collection area 21 is 1.5 liters per minute (hereinafter, the term "liters" is abbreviated as "L"). The flow rate of the air passing through the filter 12 at the second collection area 22 is 15.2 L per minute. The flow rate of the air entering and traveling through the nozzle 26 due to the suctioning by the suction part 13 is 16.7 L per minute. A period during which the air is passed through the first and second collection areas 21 and 22 for the purpose of collecting particulate matter 11, is one hour. When a position at which the particulate matter 11 is collected by the first and second collection areas 21 and 22 is referred to as a "collection position" 39, each collection area moves, after the collection has ended, from the collection position 39 to a downstream side X1 of the moving direction of the filter 12. Accordingly, a portion, of the filter 12 formed in a tape-like shape, located on an upstream side X2 of the moving direction of the filter 12 moves to the collection position 39, and stays at the collection position 39 during a period, for example one hour, during which the next collection is performed.

The measurement part 16 further includes beta ray emitters 42 and beta ray receiving/measuring sections 44. Each beta ray emitter 42 emits a beta ray to a portion, of the filter 12, onto which the particulate matter 11 is adsorbed. Each beta ray receiving/measuring section 44 receives a beta ray which has been emitted by a corresponding beta ray emitter 42 and which has been transmitted through the filter 12, and measures the amount of the beta ray. The measurement part 16 measures the mass of the particulate matter 11 adsorbed onto the filter 12, by using a beta ray absorption method, and outputs the measurement result of the mass of the particulate matter 11. The recording part 17 records the measurement result of the mass, which is outputted from the measurement part 16.

To be specific, the first and second collection areas 21 and 22 are irradiated with beta rays, respectively. Each beta ray is emitted from promethium-147, and the first and second collection areas 21 and 22 are always irradiated with the beta rays. In the case where the amount of beta ray transmitted through the filter 12 when the particulate matter 11 is not adhered to the filter 12 is set as a beta ray amount reference value, if the amount of transmission of each beta ray through the filter 12 is continuously measured, then the amount of transmission of each beta ray attenuates in accordance with an increase in the amount of particulate matter 11 collected at the corresponding collection area 20. An amount by which the amount of beta ray transmission attenuates from the beta ray amount reference value is proportional to the mass of the particulate matter 11 having been collected at the corresponding collection area 20.

Based on the above, the mass of the particulate matter 11 having been collected at each collection area 20 can be measured. The recording part 17 may record the attenuation amount of the beta ray transmission once an hour, for example, or may always record the attenuation amount. In the case where the recording part 17 always records the attenuation amount, temporal changes in the amount of suspended particulate matter in the atmosphere can be measured in such smallest possible units of time that a significant change in the mass of the particulate matter 11 collected at each collection area 20 can be observed per unit time.

In the present embodiment, the measurement part 16 further includes an optical black carbon amount measurement part 15. The optical black carbon amount measurement part 15 measures the amount of optical black carbon (hereinafter, abbreviated as "OBC") present on the collection areas 20 of the filter 12. Since OBC is usually contained in fine particles, OBC measurement is performed for the second collection area 22 that collects fine particles. OBC is measured using a nondestructive measurement method. Therefore, the measurement can be performed while the particulate matter is being collected by the filter 12. Further, the measurement of the mass of the particulate matter 11 by the beta ray absorption method can be performed in parallel with the OBC measurement.

The optical black carbon amount measurement part 15 includes a light emitter for emitting light and a reflected light detector for detecting reflected light. The greater the amount of OBC having been collected by the filter 12, the more the reflected light attenuates. The light emitter and the reflected light detector are integrated within the optical black carbon amount measurement part 15. The optical black carbon amount measurement part 15 measures the intensity of light reflected by the OBC on the filter 12, thereby measuring the amount of the OBC.

The suspended particulate matter measurement apparatus 10 is configured to further include a delay part 46. The delay part 46 is located at a position which is farther toward the downstream side of the moving direction X in which the filter 12 is fed, than the collection position 39 where the suction part 13 performs air filtration, and which is farther toward the upstream side of the moving direction X, than the position where the particulate matter 11 is dissolved in a solvent. The delay part 46 partly delays the movement of the filter 12 along the moving direction X.

The delay part 46 includes three rolls that are arranged in line at different positions along the moving direction X of the film (i.e., the filter 12). Each roll is disposed so as to be rotatable around an axis that extends perpendicularly to the moving direction X and that extends in parallel with the tape-like film. Among the three rolls, a first roll 48 that is the farthest toward the upstream side X2 of the moving direction, and a second roll 49 that is the farthest toward the downstream side X1 of the moving direction, are fixed. A third roll 51 is located between the first roll 48 and the second roll 49 with respect to the moving direction X. The third roll 51 is provided so as to be displaceable by a displacement driver. The first roll 48 and the second roll 49 are arranged near the position of the film, so as to be located on the same side with respect to the film. The third roll 51 is disposed at the opposite side to the first and second rolls 48 and 49 with respect to the film.

A state where the film is placed in a plane-like manner so as to extend from a position near the first roll 48 to a position near the second roll 49, is referred to as a "natural state" of the film. Directions perpendicular to the film in the natural state are referred to as "perpendicular directions" Z. Among the perpendicular directions Z, a direction advancing from the side on which the third roll 51 is located to the side on which the first and second rolls 48 and 49 are located is referred to as "one perpendicular direction" Z1, and a direction reverse to the one perpendicular direction Z1 is referred to as "the other perpendicular direction" Z2.

In the natural state, the third roll 51 is spaced apart in the other perpendicular direction Z2 from the first and second rolls 48 and 49. With respect to the moving direction X, the location of the third roll 51 is spaced apart from each of the first and second rolls 48 and 49 by a distance that is equal to or greater than the thickness of the film. The third roll 51, which is located between the first and second rolls 48 and 49 with respect to the moving direction X, is displaceable in the perpendicular directions Z such that the third roll 51 does not contact the first roll 48 or the second roll 49. The third roll 51 in the natural state is displaceable in the one perpendicular direction Z1.

When the third roll 51 is displaced in the one perpendicular direction Z1, a portion of the film, which is contacted by the third roll 51, is displaced in the one perpendicular direction Z1 due to the force of the third roll 51. When this state is referred to as a "displaced state" of the film, the film in the displaced state is bent at portions at which the film contacts the rolls. In the displaced state, a portion of the film, which is located between a portion contacting the first roll 48 and a portion contacting the second roll 49, is bent around the third roll 51.

The length of the film between the portion thereof, which contacts the first roll 48 from the other perpendicular direction Z2 side, and a portion thereof, which contacts the second roll 49 from the other perpendicular direction Z2 side, is different between the natural state and the displaced state. When this difference is referred to as a "setting length", the setting length is equivalent to a length of the film between the central position of the first collection area 21 and the central position of the second collection area 22.

Described below is delaying, by means of the delay part 46, a part of the movement of the filter 12 along the moving direction X. First, the collection of the particulate matter 11 at the two collection areas 20 is ended. Then, the second collection area 22 that is located farther toward the upstream side X2 of the moving direction than the first collection area 21, is moved to the extraction part 14. Next, the third roll 51 is displaced in the one perpendicular direction Z1, whereby the film enters the displaced state. Here, the third roll 51 is displaced such that a portion of the filter 12, which is located farther toward the upstream side X2 of the moving direction than the first roll 48, is not moved from the collection position 39. Accordingly, a portion of the tape-like filter 12, which is located father toward the downstream side X1 of the moving direction than the second roll 49, is sent back toward the upstream side X2 of the moving direction by the setting length. As a result, the first collection area 21 is disposed at the extraction part 14.

Next, a solvent is caused to contact the first collection area 21, and thereby the particulate matter 11 collected at the first collection area 21 is extracted and the components of the particulate matter 11 are dissolved in the solvent. Then, the resultant solution is collected. Next, the third roll 51 is displaced to return the filter 12 to the natural state, whereby the filter 12 is moved toward the downstream side such that a portion of the filter 12, the portion having the setting length, moves beyond the second roll 49. As a result, the second collection area 22 is disposed at the extraction part 14. Thus, even if the third roll 51 is displaced and the state of the filter 12 is consequently switched between the natural state and the displaced state, a portion of the filter 12, which is located farther toward the upstream side than the first roll 48, does not move in the moving direction X. Therefore, the next collection of particulate matter 11 can be performed by the filter 12 at the portion that is located farther toward the upstream side than the first roll 48, during a period during which the components of the particulate matter 11 collected at the first collection area 21 and the components of the particulate matter 11 collected at the second collection area 22 are extracted.

At the extraction part 14, a solvent of 300 μL is caused to contact each of the first and second collection areas 21 and 22. In the present embodiment, the solvent that contacts the collection areas 20 for cleansing the filter 12 is water. However, in another embodiment, the solvent may partly include an organic solvent by such an amount as to allow the pH of the solvent to be measurable. In the present embodiment, solutions, in which the particulate matter 11 collected at the collection areas 20 is dissolved as a result of the solvent having contacted the collection areas 20 and thereby cleansed the filter 12, are each conveyed to a measurement cell 54 located within the measurement part 16. In the measurement cell 54, a solvent is added to each solution such that the entire amount of each solution becomes exactly 1 mL.

In the present embodiment, the measurement part 16 measures the amount of nitrate ion, the amount of water-soluble organic matter, and the amount of sulfate ion, which are contained in the solution, and measures the acidity of the solution. To be specific, the measurement part 16 measures the amount of nitrate ion by using an absorbance method with which to measure absorbances of the solution at predetermined wavelengths. The measurement part 16 also measures the amount of water-soluble organic matter by using an absorbance method with which to measure an absorbance of the solution at a predetermined wavelength. The measurement part 16 further measures the acidity of particulate matter contained in the atmosphere, by measuring the pH of the solution. To be specific, after a pH indicator being added to the solution, the measurement part 16 measures absorbances of the solution by an absorbance method with which to measure the absorbances at particular wavelengths, thereby measuring the pH of the solution and determining the acidity of the particulate matter. Then, the measurement part 16 measures the amount of sulfate ion by barium sulfate turbidimetry. The measurement part 16 outputs measurement results indicating the amount of nitrate ion, the amount of water-soluble organic matter, and the amount of sulfate ion, which are contained in the solution, and the acidity of the solution. The recording part 17 records these measurement results outputted from the measurement part 16.

The measurement part 16 includes the measurement cell 54, a bottom part driver 56, a stirrer 57, an ultraviolet-visible light emitter 58, a spectroscopic analyzer 62, and reagent adders 63. The measurement cell 54 includes a quartz cell 66 and a bottom part 68. The quartz cell 66 is a so-called four-sided cell that is formed in a square tube-like shape having a vertical axis. The bottom part 68 fits into the quartz cell 66, thereby sealing the internal space of the quartz cell 66. The bottom part 68 is formed so as to include packing With the bottom part 68 sealing the quartz cell 66, the quartz cell 66 and the bottom part 68 retain the solution. The length of a light path of the quartz cell 66 is set to 6 mm. The depth of the solution when the solution of 1 mL is retained is set to 3 cm.

The vertical length of the quartz cell 66 is set to be equal to or greater than the double of the set depth of the solution. The stirrer 57 is, when the bottom part 68 is sealing the lower end of the quartz cell 66, disposed above the bottom part 68 so as to be spaced apart from the bottom part 68 by a distance that is greater than the depth of the solution. The stirrer 57 is realized by a mechanical stirrer. The stirrer 57 includes: a stirring rod 69 that vertically extends such that a part thereof is accommodated within the cell; a stirring motor 72, connected to the upper end of the stirring rod 69, for causing the stirring rod 69 to rotate; and a blade 74 attached to the bottom end of the stirring rod 69.

Figure 3:
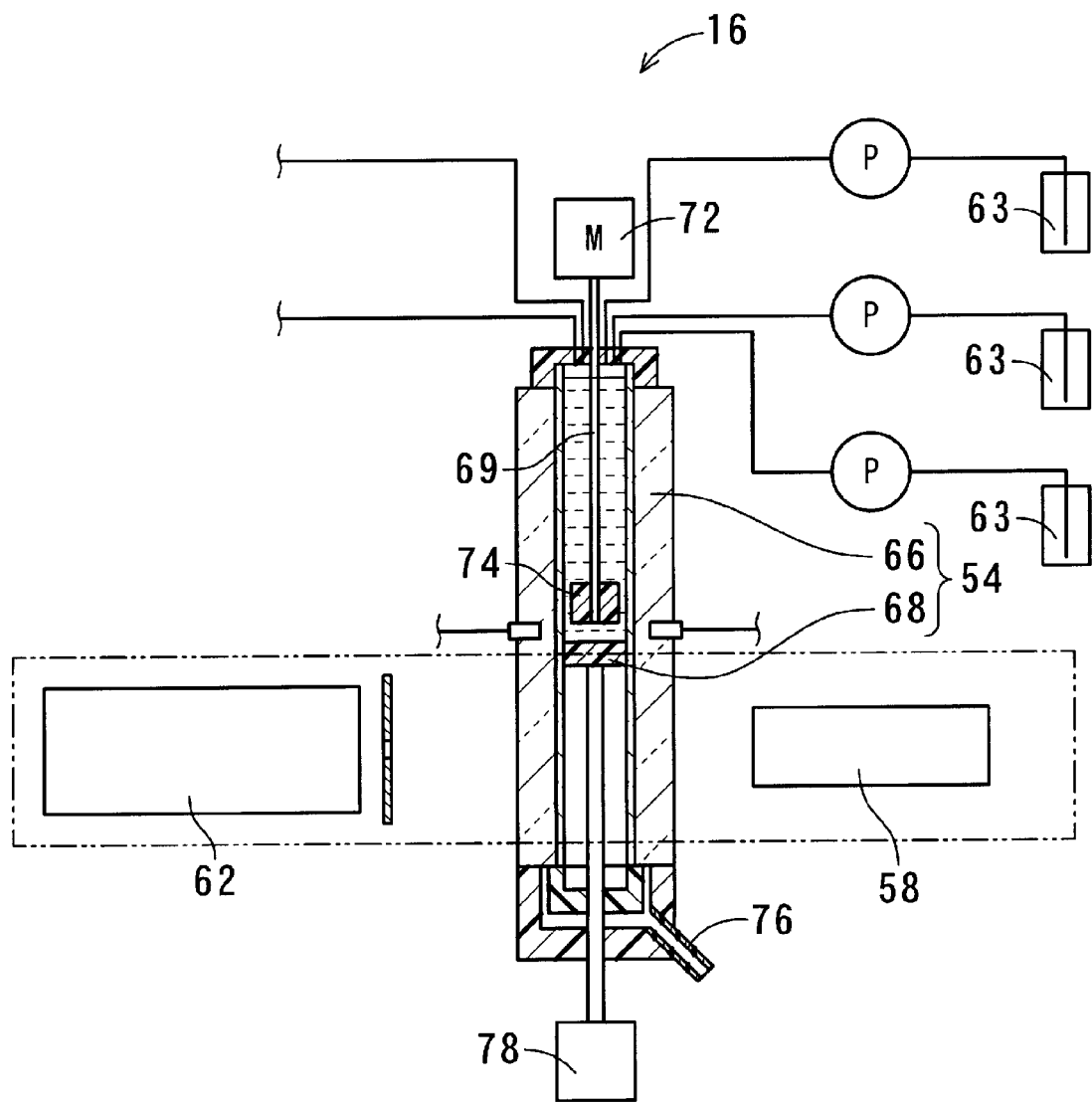
FIG. 3 is a cross-sectional view showing a measurement part 16 of the first embodiment of the present invention, the measurement part 16 being in a stirring state.
Figure 4:
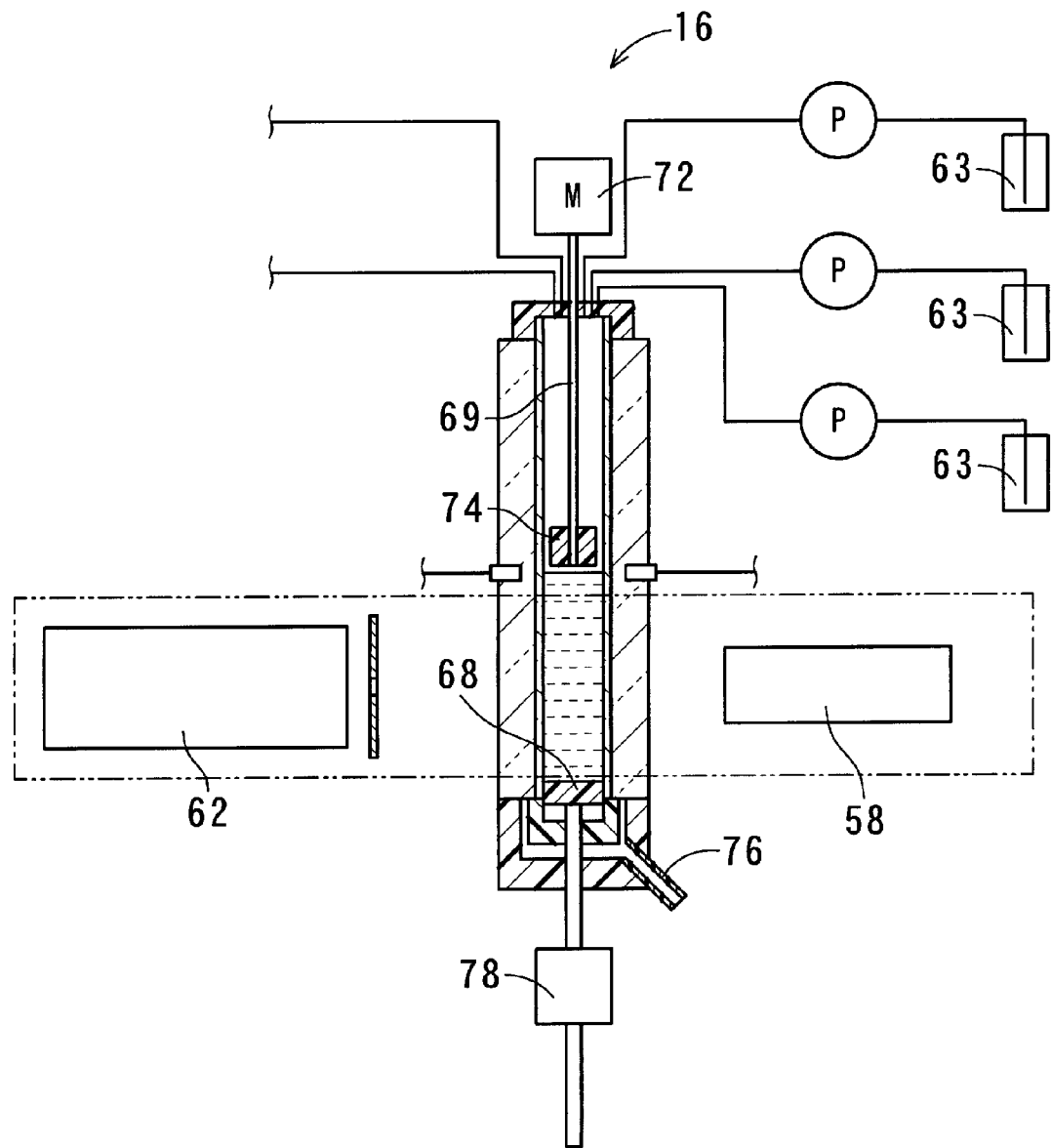
FIG. 4 is a cross-sectional view showing the measurement part 16 of the first embodiment of the present invention, the measurement part 16 being in a measuring state.
Figure 5:
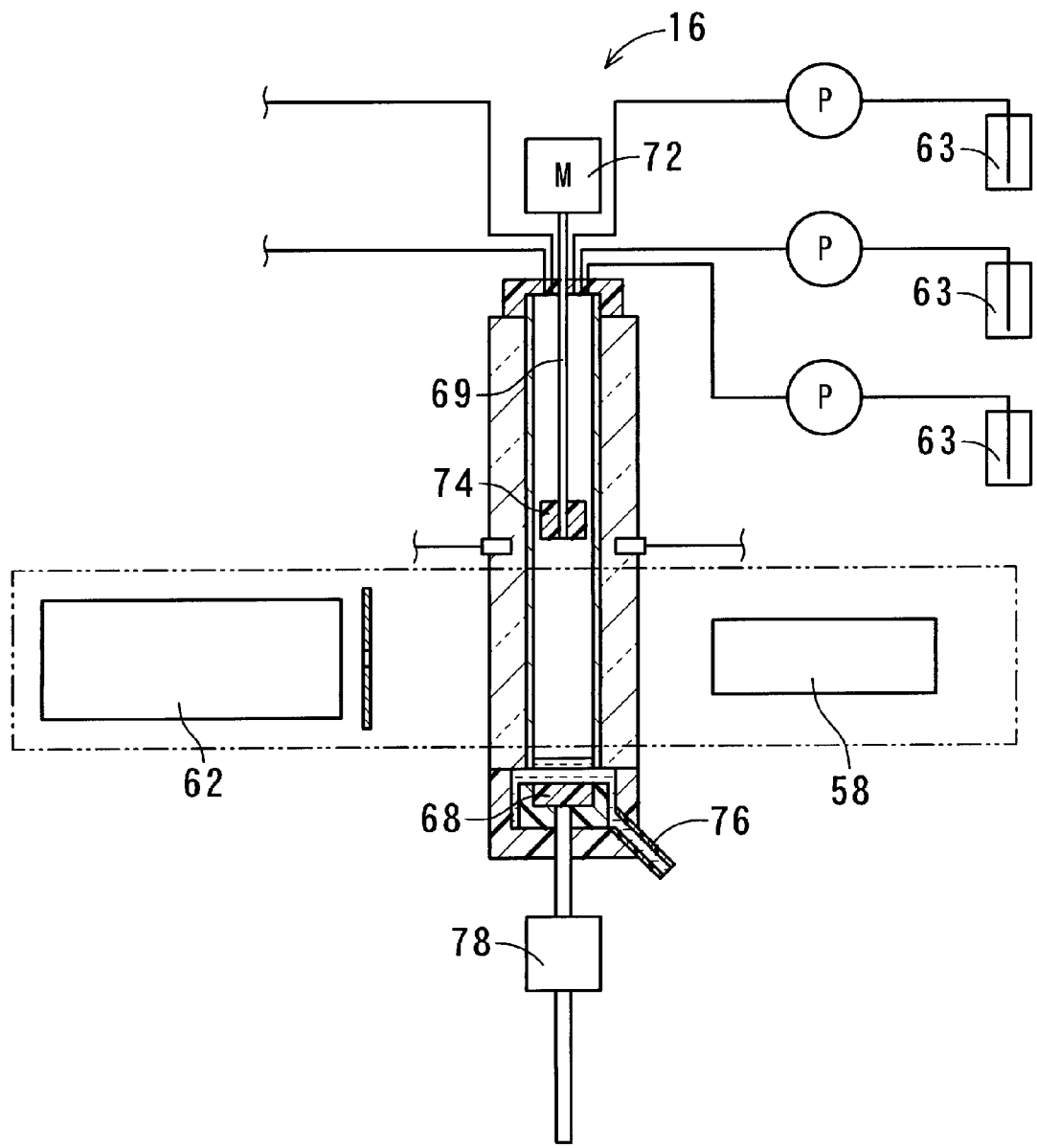
FIG. 5 is a cross-sectional view showing the measurement part 16 of the first embodiment of the present invention, the measurement part 16 being in a liquid-drainage state.

FIG. 3 is a cross-sectional view showing the measurement part 16 of the first embodiment of the present invention, the measurement part 16 being in a stirring state. FIG. 4 is a cross-sectional view showing the measurement part 16 of the first embodiment of the present invention, the measurement part 16 being in a measuring state. FIG. 5 is a cross-sectional view showing the measurement part 16 of the first embodiment of the present invention, the measurement part 16 being in a liquid-drainage state. The bottom part driver 56 includes a linear motor 78, and is capable of driving the bottom part 68 to move upward/downward. By displacing the bottom part 68, the bottom part driver 56 realizes the measuring state, the stirring state, and the liquid-drainage state.

In the measuring state, the bottom part 68 is sealing the bottom end of the quartz cell 66. In the stirring state, the bottom part 68 is disposed near and below the blade 74 that is provided at the bottom end of the stirring rod 69, and the liquid level of the solution is located above the blade 74. In the liquid-drainage state, the fitting of the bottom part 68 into the quartz cell 66 is released, and the bottom part 68 is disposed so as to be distant downward from the quartz cell 66.

In the measuring state, the solution contained in the quartz cell 66 is disposed between the ultraviolet-visible light emitter 58 and the spectroscopic analyzer 62. The ultraviolet-visible light emitter 58 and the spectroscopic analyzer 62 are realized by a UV-Vis spectrophotometer. The solution contained in the quartz cell 66 is disposed along an optical path extending from the ultraviolet-visible light emitter 58 to the spectroscopic analyzer 62. In the measuring state, the measurement part 16 measures absorbances in a visible region, an ultraviolet region, and a near-infrared region of the solution.

In the stirring state, at least the blade 74 of the stirrer 57 is submerged in the solution, and the stirring motor 72 causes the blade 74 to rotate. In this manner, the stirrer 57 stirs the solution. In the liquid-drainage state, the solution contained in the quartz cell 66 flows through a gap between the quartz cell 66 and the bottom part 68, and is thereby drained into a waste tank through a predetermined drainage path 76. In the present embodiment, the drainage path 76 is formed of a transparent material so that the solution being drained through the drainage path 76 can be viewed from the outside. Each reagent adder 63 includes a conveying pipe for conveying a predetermined amount of reagent from a container storing the reagent into the quartz cell 66. Further attached to the quartz cell 66 is a conveying pipe for conveying a predetermined amount of solvent from a container 80 storing the solvent into the quartz cell 66.

Figure 6:
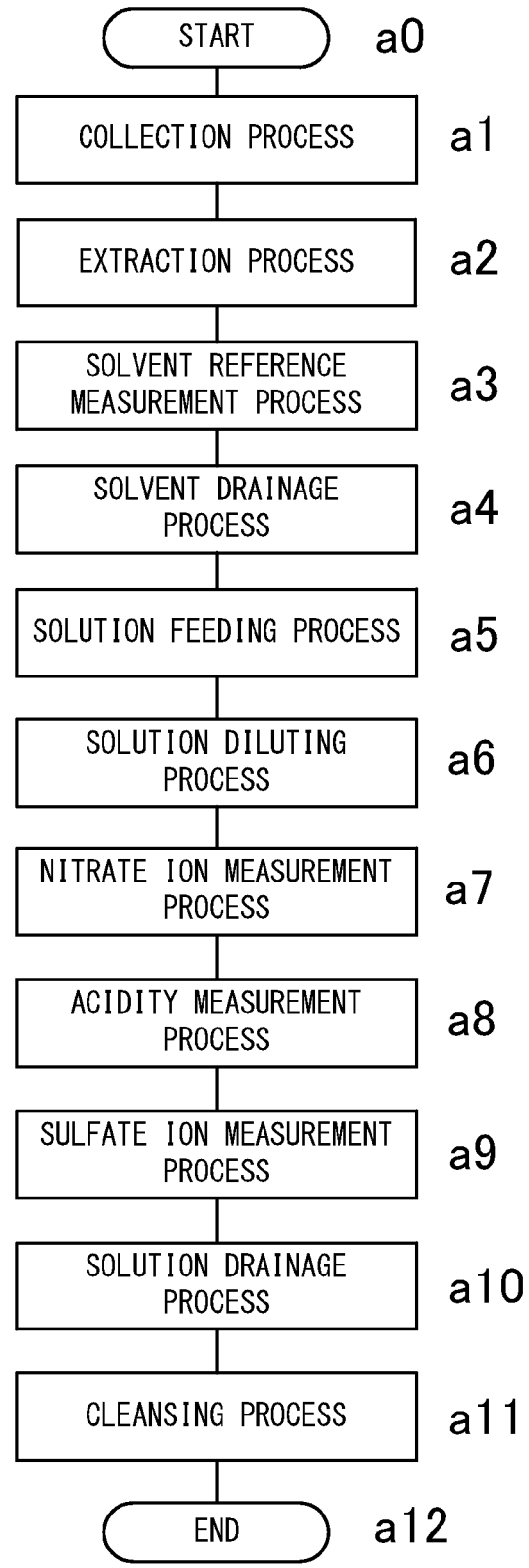
FIG. 6 is a flowchart showing processes performed in a suspended particulate matter measurement method according to the first embodiment of the present invention.

FIG. 6 is a flowchart showing processes performed in the suspended particulate matter measurement method according to the first embodiment of the present invention. The suspended particulate matter measurement method uses the suspended particulate matter measurement apparatus 10. The measurement part 16 of the suspended particulate matter measurement apparatus 10 measures the amount of nitrate ion and the amount of sulfate ion that are contained in the solution collected by the extraction part 14, and measures the acidity of the solution. The suspended particulate matter measurement method includes a nitrate ion measurement process, an acidity measurement process, and a sulfate ion measurement process.

In the nitrate ion measurement process, the amount of nitrate ion is measured using an absorbance method with which to measure absorbances of the solution at predetermined wavelengths. After the nitrate ion measurement process is performed, a pH indicator is added to the solution in the acidity measurement process. In the acidity measurement process, the acidity of particulate matter in the solution is measured based on the pH value of the solution, which pH value is measured by an absorbance method with which to measure absorbances of the solution at particular wavelengths. After the acidity measurement process is performed, the amount of sulfate ion is measured in the sulfate ion measurement process by barium sulfate turbidimetry. In the present embodiment, the measurement part 16 also measures the amount of water-soluble organic matter in the solution. In the suspended particulate matter measurement method, the amount of water-soluble organic matter is measured in the nitrate ion measurement process.

Prior to the start of performing the above processes, the measurement part 16 is in the measuring state where the quartz cell 66 has been cleansed and the bottom part 68 is fitted into the bottom end of the quartz cell 66. When the processing starts, the processing first proceeds to a collection process of step a1 at which the air in the atmosphere is suctioned and pass through the filter 12 at a constant flow rate.

In the present embodiment, the particulate matter 11 contained in the suctioned air is classified by the classification part 19 into two classes, and then collected at the two collection areas 20, respectively.

In the collection process at step a1, measurement of the mass of the particulate matter 11 by a beta ray absorption method and measurement of the amount of OBC by the optical black carbon amount measurement part 15 are performed in parallel, at the same time as the particulate matter 11 is collected. The measurement of the mass of the particulate matter 11 is performed for both the first and second collection areas 21 and 22 by the beta ray emitters 42 and the beta ray receiving/measuring sections 44. The measurement of the amount of OBC by the optical black carbon amount measurement part 15 is performed for the second collection area 22 at which fine particles are collected.

Next, the processing proceeds to an extraction process of step a2 at which the filter 12 is moved and extraction of suspended particulate matter is performed using a solvent. The filter 12 is moved until the second collection area 22 is located at the extraction part 14. Then, the third roll 51 of the delay part 46 is caused to be displaced in the one perpendicular direction Z1, whereby the first collection area 21 is located at the extraction part 14. In the extraction part 14, the solvent is caused to contact the first collection area 21, whereby the particulate matter 11 collected at the first collection area 21 is extracted and the components of the particulate matter 11 are dissolved in the solvent. Then, the resultant solution is collected.

Next, the processing proceeds to a solvent reference measurement process of step a3 at which only a solvent is fed into the quartz cell 66 and spectroscopic analysis is performed thereon so as to obtain reference values. Of the light emitted from the ultraviolet-visible light emitter 58, the optical intensity of light transmitted through the quartz cell 66 into which only the solvent has been fed, is measured at various wavelengths. The measurement results are used as a reference for subsequent measurement in which measurement results are obtained as relative values.

Next, the processing proceeds to a solvent drainage process of step a4 at which the linear motor 78 of the bottom part driver 56 is driven so as to lower the bottom part 68 such that the measurement part 16 enters the liquid-drainage state, whereby the solvent within the quartz cell 66 is drained. Subsequently, the processing proceeds to a solution feeding process of step a5 at which the bottom part 68 is displaced so as to cause the measurement part 16 to enter the measuring state, and the solution in which the particulate matter 11 is dissolved is fed into the quartz cell 66. Then, the processing proceeds to a solution diluting process of step a6 at which a solvent is fed into the quartz cell 66, and as a result of the solvent being fed thereinto, the solution within the quartz cell 66 is stirred.

Next, the processing proceeds to the nitrate ion measurement process of step a7 at which measurement is performed at predetermined wavelengths and thereby the concentration of nitrate ion in the solution is measured. Here, the predetermined wavelengths are 228 nm and 239 nm. Detailed descriptions regarding the wavelengths and the measurement will be provided below. In the nitrate ion measurement process of the present embodiment, the amount of water-soluble organic matter in the solution is also measured. The amount of water-soluble organic matter is measured through absorbance measurement at a predetermined wavelength. The predetermined wavelength is 254 nm.

Next, the processing proceeds to the acidity measurement process of step a8 at which the solution is stirred, a pH indicator is fed into the quartz cell 66, and absorbances of the solution are measured. In order for the solution to be stirred, the linear motor 78 causes the bottom part 68 to be displaced such that the measurement part 16 enters the stirring state, and the stirring motor 72 causes the stirring rod 69 to rotate. As a result, the blade 74 rotates in the solution and thereby the solution is stirred. When the solution is being stirred, a pH indicator is fed thereinto. The pH indicator used herein is bromophenol blue, and the amount of bromophenol blue to be added is 10 μL. Then, the bottom part driver 56 is driven so as to cause the measurement part 16 to enter the measuring state and perform spectroscopic analysis. The UV-Vis absorption spectrum of bromophenol blue varies depending on a variation of the pH of the solution. Bromophenol blue has an isosbestic point at the wavelength of 495 nm. In a wavelength region equal to or greater than 680 nm, bromophenol blue has no absorption whatever the pH of the solution is. Wavelengths to be used in the measurement and the details of the measurement will be described below.

Subsequently, the processing proceeds to the sulfate ion measurement process of step a9 at which the solution is stirred, barium chloride is added to the solution, and measurement of transmitted light intensity is performed. The solution is stirred in the same manner as in the acidity measurement process of step a8. Barium chloride is added to the solution being stirred. The amount of barium chloride to be added is set to an amount that is sufficient relative to the amount of sulfate ion in the solution and that is dissolvable in the solution. The concentration of sulfate ion is measured using the ultraviolet-visible light emitter 58 and the spectroscopic analyzer 62. The measurement of the concentration is performed by comparing the transmitted light intensity measured before barium chloride is added to the solution and the transmitted light intensity measured after barium chloride is added to the solution and the solution is stirred.

In the case where barium chloride is added to the solution when sulfate ion is contained in the solution, barium sulfate is formed and suspended in the solution. In the present embodiment, the concentration range of sulfate ion in the quartz cell 66 is no less than 10 μmol/L and no greater than 100 μmol/L. In this concentration range, a rate at which the transmitted light intensity decreases after the addition of barium chloride from the transmitted light intensity obtained prior to the addition of barium chloride, is proportional to the concentration of sulfate ion. Hereinafter, the unit "μmol/L" may be alternatively indicated as "μM". Here, a wavelength at which the transmitted light intensity is measured is 495 nm at which bromophenol blue shows an isosbestic point, or is a wavelength within a wavelength region equal to or greater than 680 nm in which bromophenol blue does not have absorption. The measurement will be described in detail below.

Next, the processing proceeds to a solution drainage process of step a10 at which the solution contained in the quartz cell 66 is drained. Similarly to the drainage of the solvent in the solvent drainage process, this process is performed in the following manner: the linear motor 78 of the bottom part driver 56 causes the bottom part 68 to be displaced downward, and thereby the measurement apparatus enters the liquid-drainage state.

Subsequently, the processing proceeds to a cleansing process of step a11 at which the quartz cell 66, the bottom part 68, and the drainage path 76 are cleansed using a solvent. The bottom part driver 56 causes the bottom part 68 to fit into the bottom end of the quartz cell 66, and the measurement part 16 enters the measuring state, accordingly. When the measurement part 16 has entered the measuring state, the solvent is fed into the quartz cell 66. Thereafter, the bottom part driver 56 causes the bottom part 68 to be lifted to the vicinity of, but below, the stirrer 57. Accordingly, the blade 74 and a part of the stirring rod 69 are submerged in the solvent. In this state, the stirring rod 69 is rotated to cleanse the stirrer 57. Thereafter, the bottom part driver 56 lowers the bottom part 68 to the height of the bottom end of the quartz cell 66, and further causes the fitting of the bottom part 68 into the quartz cell 66 to be released. As a result, the solvent is drained. Since the bottom part 68 is lifted and lowered while being in contact with the inner wall of the quartz cell 66 via the packing, the inner wall of the quartz cell 66 can be cleansed by the solvent and the packing.

In this cleansing process, the cleansing of the quartz cell 66 and the stirrer 57 is completed after repeating the feeding and draining of the solvent a plurality of times. Thereafter, the cleansing process ends. The suspended particulate matter measurement method shown in the flowchart of FIG. 6 is completed in approximately 10 minutes for one collection area 20. Since there are two collection areas 20 in the present embodiment, the processing is repeated twice. The period during which the particulate matter 11 is collected from the air in the atmosphere at the collection areas 20 is one hour. Thus, even though the processing of FIG. 6 is performed twice, the measurement can be ended within a period that is shorter than the period for performing the collection. This makes it possible to avoid the following situation: the measurement part 16 is still performing the measurement when the next collection at the collection areas 20 has been completed, and therefore, the collection areas 20 are left until the measurement part 16 completes the measurement.

The processing according to the flowchart shown in FIG. 6, the movement of the filter 12, the driving of the delay part 46, each operation of the measurement part 16, and the recording of the measurement results, are controlled by, for example, a computer that includes a central processing unit (CPU). Such control operations by the computer are realized by a program or the like which stores a control method to be performed by the computer and which is in a format readable by electronic components including the CPU.

Figure 7:
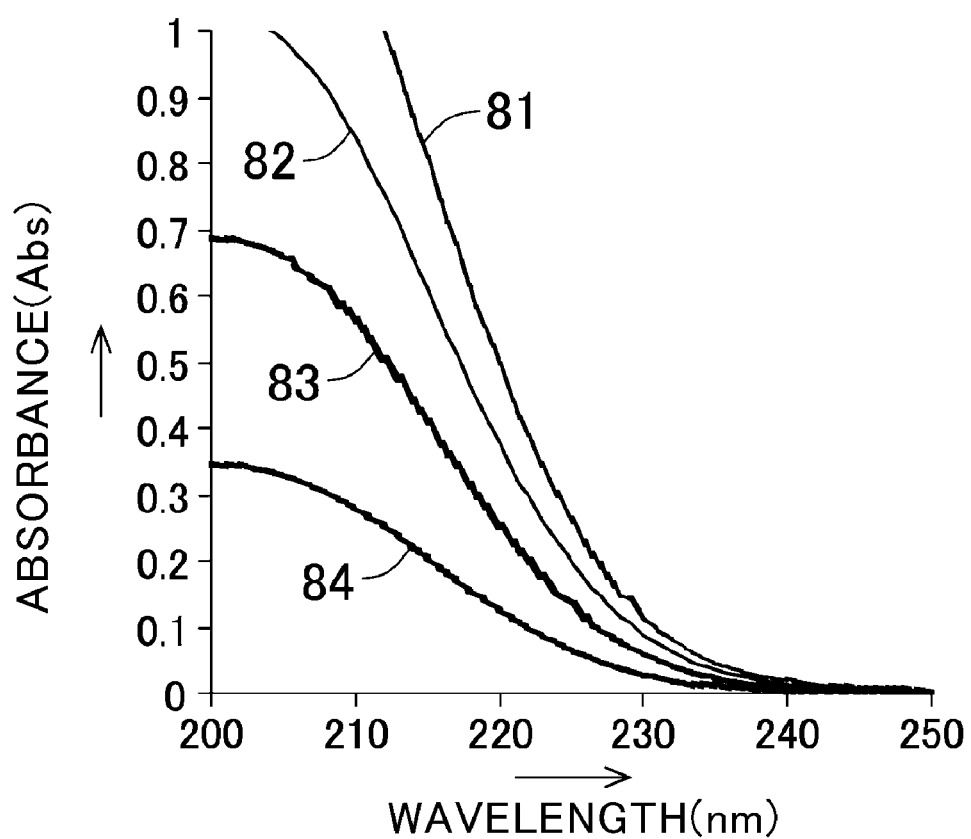
FIG. 7 shows absorption spectra of nitrate ion.

FIG. 7 shows absorption spectra of nitrate ion. In FIG. 7, the horizontal axis represents wavelength at which absorbance measurement is performed, and the vertical axis represents absorbance. When these spectra are referred to as first, second, third, and fourth spectra 81, 82, 83, and 84 from the topmost spectrum in FIG. 7 in said order, the first spectrum 81 shows absorbances when the concentration of nitrate ion in the quartz cell 66 is 143 μM; the second spectrum 82 shows absorbances when the concentration of nitrate ion in the quartz cell 66 is 107 μM; the third spectrum 83 shows absorbances when the concentration of nitrate ion in the quartz cell 66 is 71 μM; and the fourth spectrum 84 shows absorbances when the concentration of nitrate ion in the quartz cell 66 is 36 μM.

Although each absorbance spectrum of nitrate ion is peaked at approximately 200 nm, if a xenon flash lamp is used as the ultraviolet-visible light emitter 58, light intensity is small in a wavelength region equal to or less than approximately 220 nm. Therefore, in order to reduce measurement errors, it is preferred that the absorbance measurement is performed in a wavelength region greater than 220 nm. In a wavelength region greater than 240 nm, the molar absorption coefficient of nitrate ion is small, and accordingly, measurement of the concentration of nitrate ion based on absorbance measurement is difficult. Therefore, in the present embodiment, the absorbance measurement is performed at two wavelengths that are 228 nm and 239 nm. In particular, between a nitrate ion concentration and a value that is obtained by deducting the absorbance at 239 nm from the absorbance at 228 nm, there is a favorable linear relationship that can serve as an indicator that indicates a nitrate ion concentration with little error.

In the case where water is used as the solvent, the molar absorption coefficient of nitrate ion at 228 nm is $\epsilon=1060$ cm$^{-1}$ mol$^{-1}$ L, and the molar absorption coefficient of nitrate ion at 239 nm is $\epsilon=130$ cm$^{-1}$ mol$^{-1}$ L. Thus, by determining the amount of nitrate ion contained in the solution based on the absorbances at the plurality of wavelengths, the amount of contained nitrate ion can be measured with little error.

Figure 8:
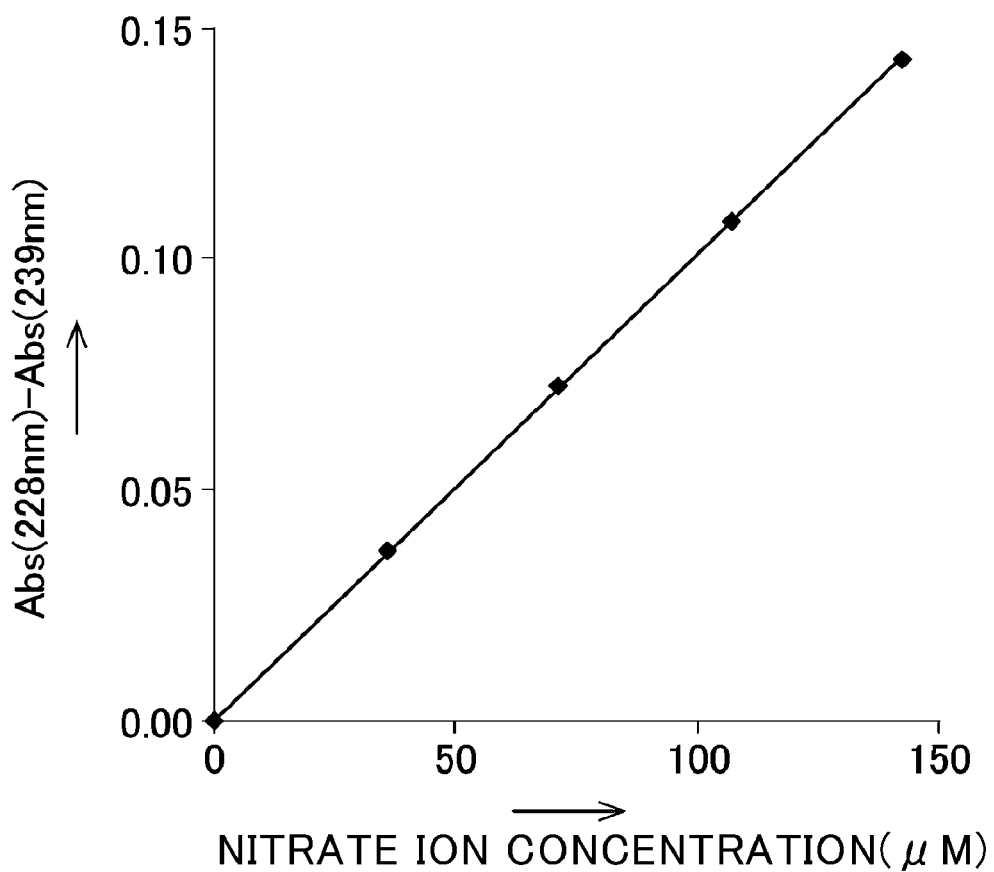
FIG. 8 shows a relationship between the concentration of nitrate ion and a value resulting from deducting an absorbance at 239 nm from an absorbance at 228 nm.

FIG. 8 shows a relationship between the concentration of nitrate ion and the value resulting from deducting the absorbance at 239 nm from the absorbance at 228 nm. The horizontal axis represents the concentration of nitrate ion in a unit "µM", and the vertical axis represents the difference between the absorbances (in a dimensionless unit). This is used as a calibration curve, which allows the concentration of nitrate ion in the quartz cell 66 to be measured with high precision in units of several tens of µM.

Figure 9:
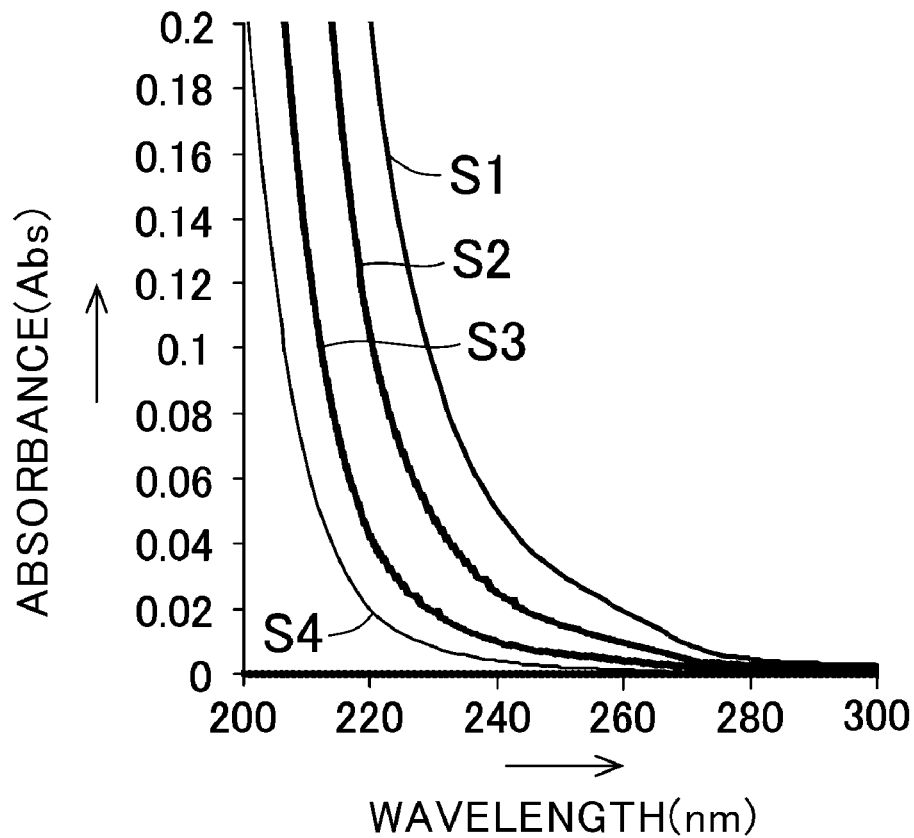
FIG. 9 shows UV-Vis absorption spectra in the case where water-soluble organic matter is contained in addition to nitrate ion.

FIG. 9 shows UV-Vis absorption spectra of oxalic acid that is water-soluble organic matter. When these spectra are referred to as first, second, third, and fourth organic matter spectra S1, S2, S3, and S4 from the topmost and rightmost spectrum in FIG. 9 in said order, the first organic matter spectrum S1 is an absorption spectrum of an aqueous solution of which the oxalic acid concentration is 1000 µM; the second organic matter spectrum S2 is an absorption spectrum of an aqueous solution of which the oxalic acid concentration is 500 µM; the third organic matter spectrum S3 is an absorption spectrum of an aqueous solution of which the oxalic acid concentration is 200 µM; and the fourth organic matter spectrum S4 is an absorption spectrum of an aqueous solution of which the oxalic acid concentration is 100 µM.

Each UV-Vis absorption spectrum of water-soluble organic matter shows absorption at 254 nm at which nitrate ion does not show absorption. None of the water-soluble organic matters shows absorption in a wavelength region equal to or greater than 680 nm. Accordingly, the amount of water-soluble organic matter contained in each aqueous solution can be determined by using the absorbance at 254 nm or by using a difference between the absorbance at 254 nm and the absorbance at 680 nm. Although each water-soluble organic matter shows absorption at 228 nm and 239 nm that are used in the calculation of the amount of contained nitrate ion, the amount of contained nitrate ion can be precisely determined by determining the amount of contained water-soluble organic matter based on the absorbance at 254 nm at which nitrate ion does not show absorption.

Figure 10:
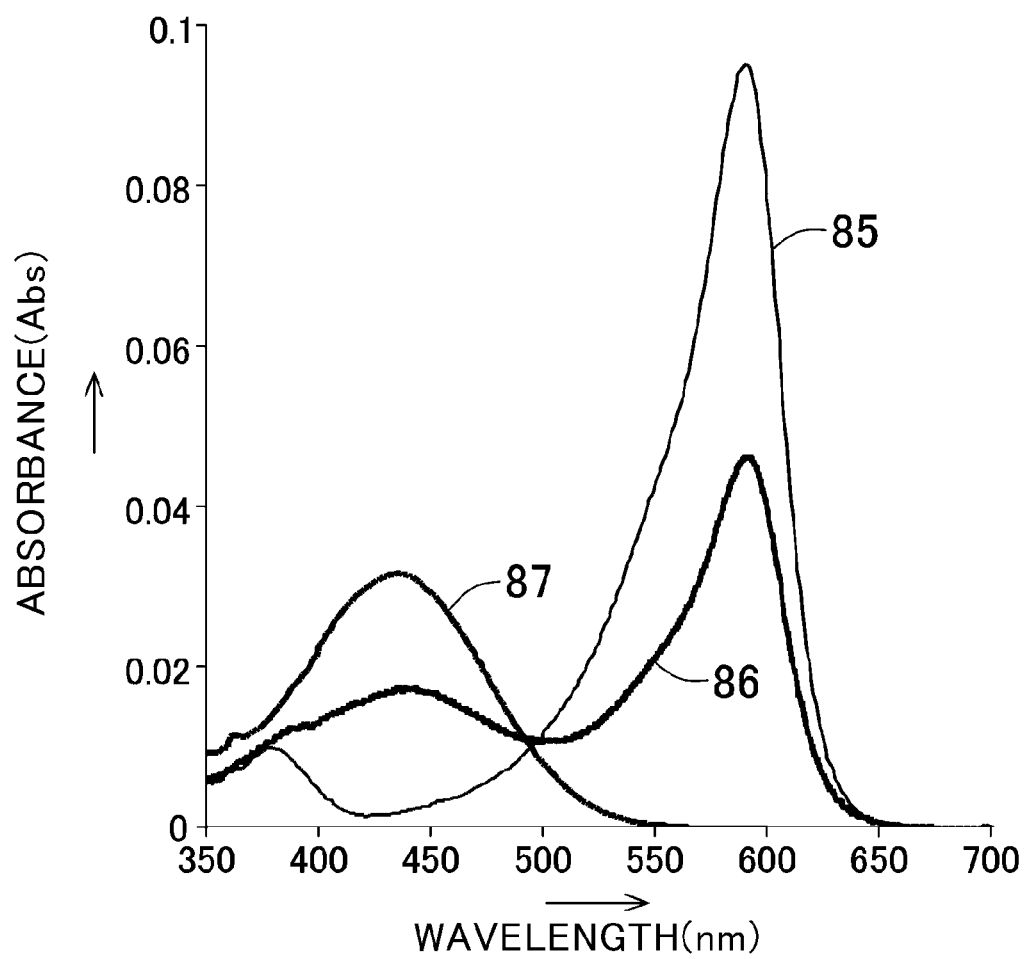
FIG. 10 shows UV-Vis absorption spectra of solutions having various hydrogen ion concentrations (pH), in each of which bromophenol blue is dissolved.

FIG. 10 shows UV-Vis absorption spectra of solutions having various hydrogen ion concentrations (pH), in each of which bromophenol blue is dissolved. FIG. 10 shows UV-Vis absorption spectra that are obtained in relation to various pH values under the condition that the concentration of bromophenol blue in the quartz cell 66 is 1.49 µM. When these spectra are referred to as fifth, sixth, and seventh spectra 85, 86, and 87 from the topmost spectrum at 590 nm in FIG. 10 in said order, the fifth spectrum 85 is a spectrum obtained under the condition that the concentration of hydrochloric acid is 0.2 mol/L and the pH is 0.7. Here, the unit "mol/L" may be alternatively indicated as "M". The sixth spectrum 86 is a spectrum obtained under the condition that the concentration of potassium hydrogen phthalate is 0.05M and the pH is 4.01. The seventh spectrum 87 is a spectrum obtained under the condition that potassium dihydrogen phosphate and sodium dihydrogen phosphate are both dissolved at the concentration of 0.025 and the pH is 6.86.

When water is used as a solvent, bromophenol blue shows the maximum absorption at 435 nm under an acid condition, and shows the maximum absorption at 590 nm under a neutral to alkaline condition. The molar absorption coefficient at the isosbestic point of 495 nm is $\epsilon=7000$ cm$^{-1}$ mol$^{-1}$ L. The absorbance at this wavelength does not depend on the pH of the solution. The pH of the solution can be measured more accurately if carbon dioxide ($CO_2$) is not contained in the water that is used as the solvent. However, when the pH value of the solution is less than 4.5, the effect of dissolved carbon dioxide can be ignored. When the temperature and the conditions for stirring are constant, the effect of carbon dioxide on the pH value of the solution is also constant. Accordingly, the effect of carbon dioxide can be calculated, by measuring the pH, adjusted to a known pH, of the solution in the same manner as that used in the measurement of particulate matter and by collecting fundamental data. Therefore, the effect of carbon dioxide can be corrected whatever the pH of the solution is.

Figure 11:
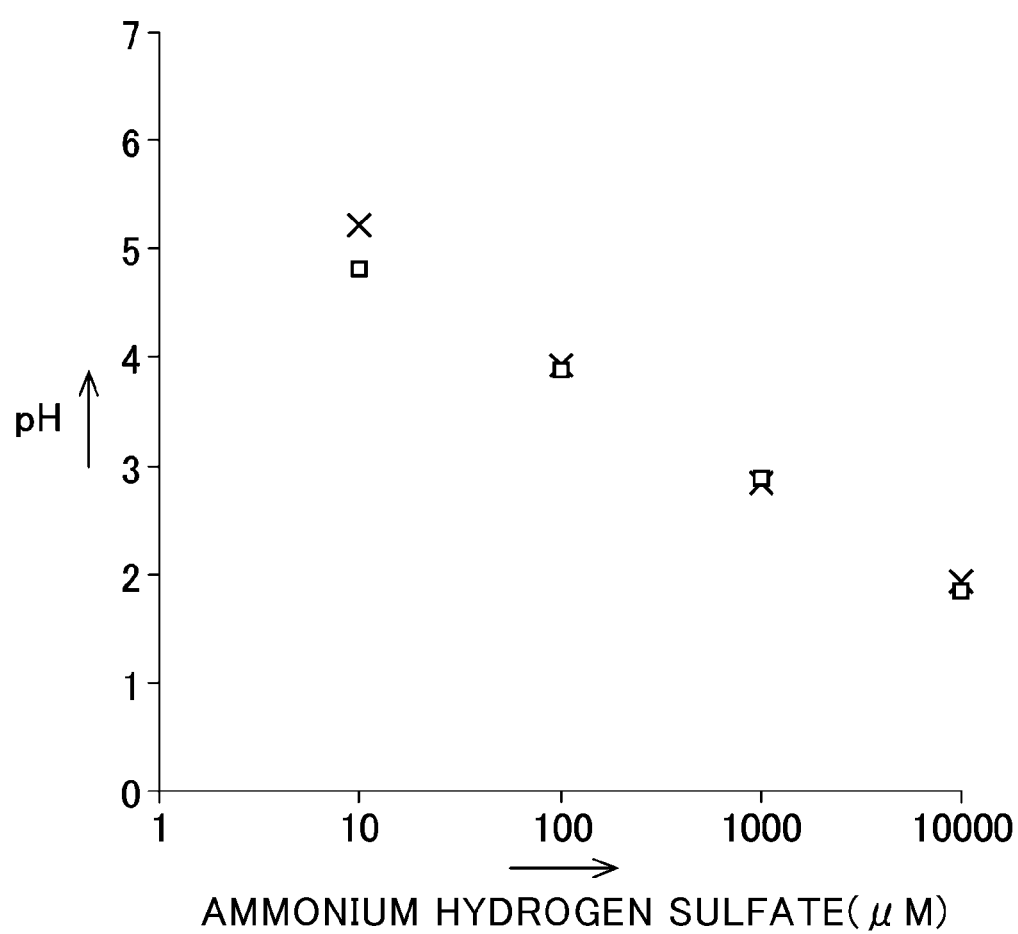
FIG. 11 shows measurement results of the pH of a solution when the pH is measured in the first embodiment, and shows measurement results of the pH of the same solution when the pH is measured using a pH electrode.

FIG. 11 shows measurement results of the pH of a solution when the pH is measured in the first embodiment, and shows measurement results of the pH of the same solution when the pH is measured using a pH electrode. Plotted as squares are the measurement results according to the present embodiment, and plotted as crosses are the measurement results obtained through the measurement using the pH electrode. As shown in FIG. 11, the results of the pH measurement in the present embodiment and the results of the pH measurement using the pH electrode substantially coincide with each other. In the present embodiment, the pH of the solution can be determined accurately by measuring a difference between the absorbance at 435 nm and the absorbance at 495 nm, or by measuring a difference between the absorbance at 590 nm and the absorbance at 495 nm. In place of the absorbance at 495 nm, an absorbance at any wavelength equal to or greater than 680 nm, at which bromophenol blue does not show absorption, may be used. By measuring the pH of the solution by using absorbances at a plurality of wavelengths in the above manner, pH measurement can be performed with little error. Accordingly, the acidity of the particulate matter in the solution can be determined.

Figure 12:
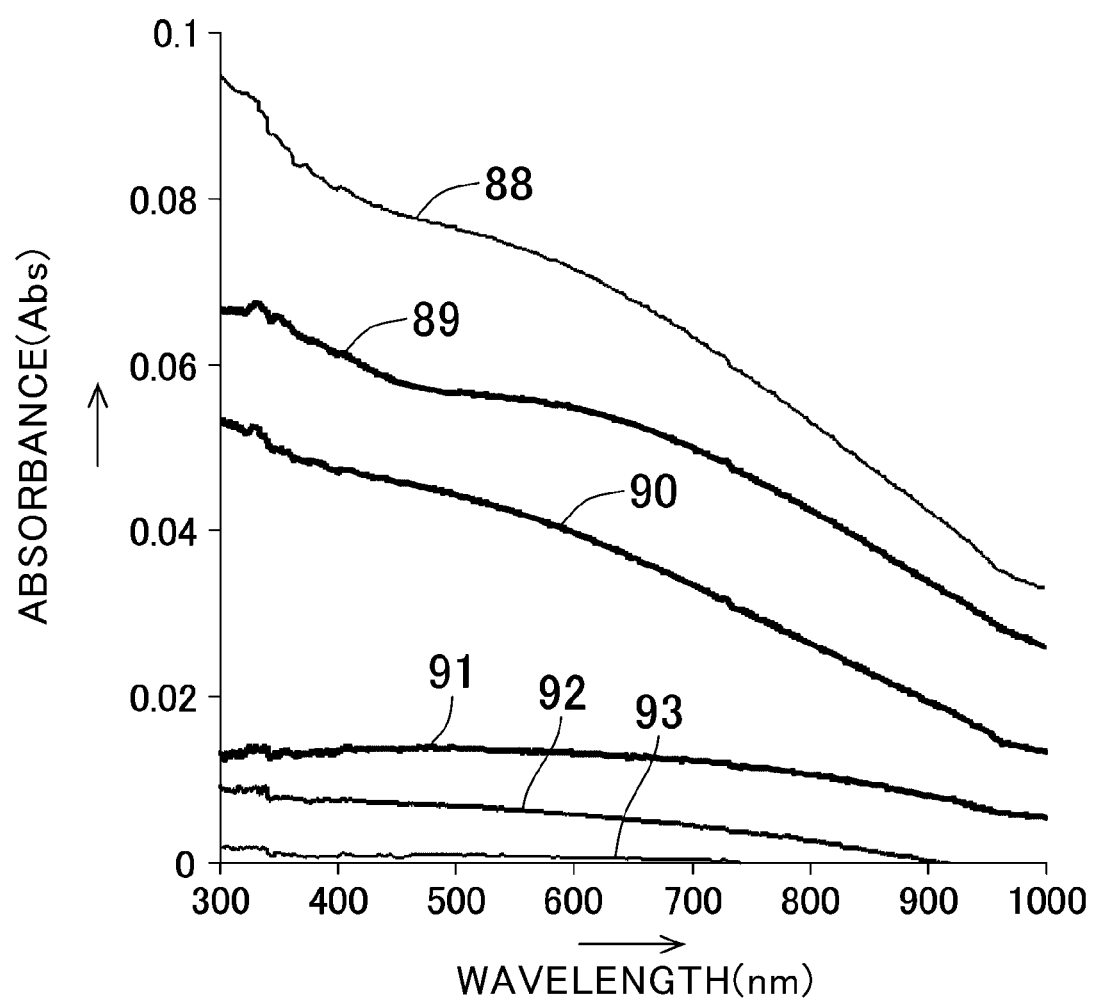
FIG. 12 shows spectra of transmitted light intensities in the case where barium sulfate is dispersed in water.

FIG. 12 shows spectra of transmitted light intensities in the case where barium sulfate is dispersed in water. When these spectra are referred to as eighth, ninth, tenth, eleventh, twelfth, and thirteenth spectra 88, 89, 90, 91, 92, and 93 from the topmost spectrum in FIG. 12 in said order, the eighth spectrum 88 is a spectrum of transmitted light intensity in the case where barium sulfate is dispersed in the water in such an amount that the concentration thereof is 100 µM if fully dissolved in the water, and the ninth spectrum 89 is a spectrum of transmitted light intensity in the case where barium sulfate is dispersed in the water in such an amount that the concentration thereof is 82 µM if fully dissolved in the water.

The tenth spectrum 90 is a spectrum of transmitted light intensity in the case where barium sulfate is dispersed in the water in such an amount that the concentration thereof is 51 µM if fully dissolved in the water; the eleventh spectrum 91 is a spectrum of transmitted light intensity in the case where barium sulfate is dispersed in the water in such an amount that the concentration thereof is 30 µM if fully dissolved in the water; the twelfth spectrum 92 is a spectrum of transmitted light intensity in the case where barium sulfate is dispersed in the water in such an amount that the concentration thereof is 10 µM if fully dissolved in the water; the thirteenth spectrum 93 is a spectrum of transmitted light intensity in the case where barium sulfate is not dispersed in the water.

FIG. 13 shows a calibration curve that is obtained based on the data shown in FIG. 12. When the concentration of sulfate ion is approximately equal to or less than 120 μM that is a low concentration, it is difficult to measure the concentration of sulfate ion within a few minutes unless a turbidimetric method is used. In a turbidimetry method where barium chloride is used to form barium sulfate and a transmitted light intensity is measured, the concentration of sulfate ion can be measured within a short period of time with high precision by performing the measurement based on the calibration curve shown in FIG. 13.

In the atmosphere, there exist suspended particulate matter of various particle diameters. Among these, in particular, suspended particulate matter of which the particle diameter is equal to or less than 10 μm is, when a person breathes, inhaled and settled in the lungs without being filtered by the respiratory tract. Thus, such particulate matter is highly toxic particularly to humans. For this reason, the environmental standards for air pollution based on the Basic Act for Environmental Pollution Control define that the particle diameter of suspended particulate matter in the atmosphere is equal to or less than 10 μm. In accordance with the definition, there are conventional apparatuses available in the market which are capable of measuring the weight of suspended particulate matter of which the particle diameter is equal to or less than 10 μm. However, referred to as "suspended particulate matter" herein is not limited to particulate matter 11 of which the particle diameter is equal to or less than 10 μm, but including particulate matter 11 of which the particle diameter is greater than 10 μm.

Particles present in suspended particulate matter in the atmosphere are categorized by size, with reference to a particle diameter of approximately 2.5 μm, into coarse particles (which hereinafter may be referred to as CPs) and fine particles (which hereinafter may be referred to as FPs).

CPs include sea salt particles, dusts originating from soil, and the like that naturally exist. On the other hand, FPs include: primary particles, for example, dusts emitted from factories or the like and particles directly emitted to the atmosphere from emission sources such as diesel-powered automobiles; and secondary particles that are a result of gaseous substances such as sulfur oxides ($SO_x$), nitrogen oxides ($NO_x$), volatile organic compounds (VOC), and the like having transformed into particulate matter 11 in the atmosphere. From the results of an epidemiological investigation into the effects, on the human body, of suspended particulate matter of various particle diameters in the atmosphere in urban areas, FPs are considered to cause, even in a low concentration, diseases such as cardiovascular diseases, lung cancer, asthma, and the like, and the results show that the weight concentration of FPs is proportional to the mortality rate.

Figure 14A:
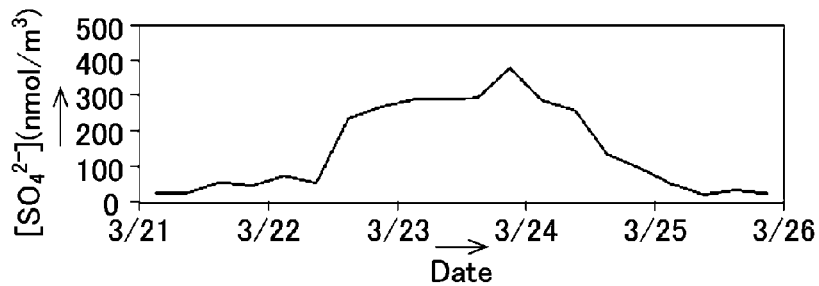
FIGS. 14A to 14E show results of measurement performed by the suspended particulate matter measurement apparatus and the suspended particulate matter measurement method according to the first embodiment of the present invention.
Figure 14B:
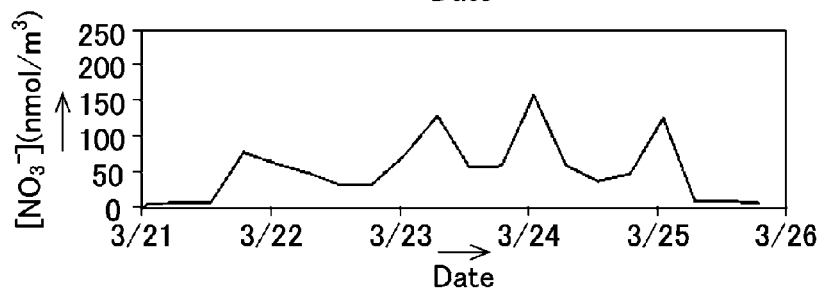
Figure 14C:
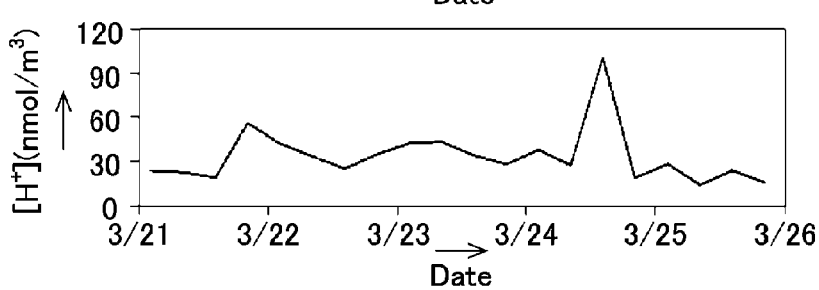
Figure 14D:
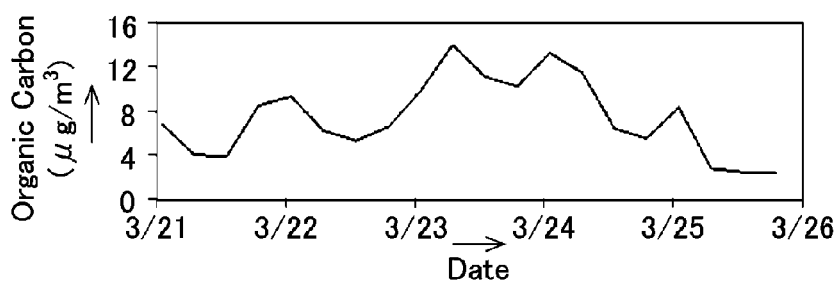
Figure 14E:
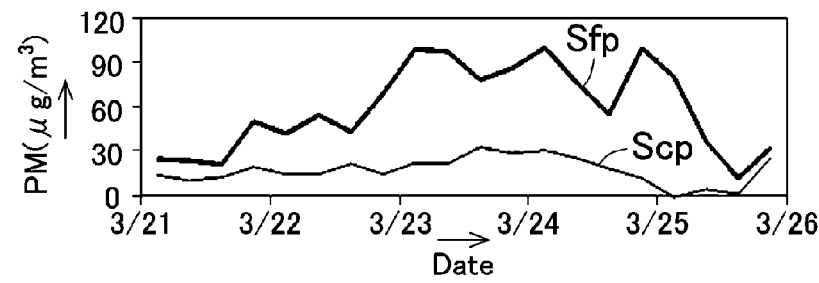

FIGS. 14A to 14E show results of measurement performed by the suspended particulate matter measurement apparatus and the suspended particulate matter measurement method according to the first embodiment of the present invention. FIG. 14A shows the amount of sulfate ion contained in fine particles; FIG. 14B shows the amount of nitrate ion contained in fine particles; FIG. 14C shows the acidity of fine particles as the amount of hydrogen ion contained in the air; FIG. 14D shows the amount of water-soluble organic matter contained in fine particles; and FIG. 14E shows the amount of coarse particles and fine particles contained in the air of the atmosphere. When the spectrum shown in the upper position in FIG. 14E is referred to as an "FP spectrum" Sfp and the spectrum shown in the lower position in FIG. 14E is referred to as a "CP spectrum" Scp, the FP spectrum Sfp represents the amount of fine particles and the CP spectrum Scp represents the amount of coarse particles.

In FIG. 14, the horizontal axis indicates dates, and the vertical axis indicates values each having been converted into an amount contained in 1 $m^3$ of air. In FIGS. 14A to 14C, the unit of the vertical axis is "$nmol/m^3$". In FIGS. 14D and 14E, the unit of the vertical axis is "$\mu g/m^3$". The suspended particulate matter measurement apparatus of the present embodiment, which is capable of performing measurement every hour, is also capable of performing measurement every few hours. Moreover, the suspended particulate matter measurement apparatus of the present embodiment is capable of performing automatic continuous measurement for a few days, as shown in FIGS. 14A to 14E.

As shown in FIG. 14E, the amount of fine particles is greater than the amount of coarse particles. In terms of harmful effects on the human body, fine particles are more harmful than coarse particles. Although FIGS. 14A to 14D only show the measurement results of fine particles, the same measurement can be performed on coarse particles. As shown in FIGS. 14A to 14E, the above multiple types of measurement can be automatically and continuously performed on suspended particulate matter in the air of the atmosphere. Accordingly, precise data on temporal changes in the suspended particulate matter can be obtained.

According to the present embodiment, the suspended particulate matter measurement apparatus 10 and the suspended particulate matter measurement method are capable of measuring such particulate matter 11 as sulfur oxides, nitrogen oxides, and volatile organic compounds mentioned above. In the suspended particulate matter measurement apparatus 10, the suction part 13 suctions the air in the atmosphere at a constant flow rate, so as to cause particulate matter 11 contained in the atmosphere to be collected by the filter 12. The extraction part 14 causes the particulate matter 11 collected by the filter 12 to be dissolved into a solvent, thereby extracting the components of the particulate matter 11, and collects the resultant solution. The measurement part 16 measures at least one of the amount of nitrate ion and the amount of sulfate ion which are contained in the solution collected by the extraction part 14, and outputs the measurement result. In this manner, the components of particulate matter 11 contained in a substantial amount of air in the atmosphere can be condensed into a small amount of solution and then collected. Accordingly, at least one of the amount of nitrate ion and the amount of sulfate ion, which are contained in particulate matter 11 in the atmosphere, can be automatically measured with high sensitivity.

By further measuring the pH of the solution, the measurement part 16 measures the acidity of particulate matter contained in the atmosphere. The recording part 17 records a result of the acidity measurement, which is outputted from the measurement part 16. In this manner, temporal changes in the amount of acid substances contained in the atmosphere and an increase/decrease of effects on the environment caused thereby can be automatically measured. This contributes to conducting investigation into, and taking measures against, the effects of suspended particulate matter on the environment, such as acid rain.

In the conventional technique, the measurement is performed after the collection of particulate matter has been performed for 24 hours. However, since the present invention can perform the measurement with high sensitivity, the measurement can be performed after the collection has been performed for approximately one hour. This reduces a time period during which the collected particulate matter 11 is exposed to the flow of air, thereby preventing chemical alteration of the particulate matter 11. Since acid components contained in particulate matter are neutralized by ammonia contained in the air of the atmosphere, such acid components are neutralized if the collection of particulate matter is performed for a long period of time. For this reason, the conventional technique, which requires the collection to be performed for a long period of time, cannot measure the acidity of particulate matter accurately. On the other hand, the suspended particulate matter measurement apparatus and the suspended particulate matter measurement method of the present embodiment can perform the measurement after performing the collection only for a short period of time. This realizes accurate particulate matter measurement.

Moreover, since the collected particulate matter may contain volatile substances, a loss of such volatile substances occurs if the collection is performed for 24 hours. On the other hand, in the present embodiment, the time period for the collection can be shortened as compared to the conventional technique. As a result, the measurement can be performed while suppressing dispersion and volatilization of substances. This allows the measurement to be performed with high precision. Further, since the recording part 17 records the measurement results, the recorded measurement results can be referenced after the measurement has been performed. Still further, the measurement apparatus, which is substantially more simplified and convenient, less expensive, and capable of performing more stable measurement than an ion chromatograph, an X-ray fluorescence spectrometer (XRF), a mass spectrometer (MS), and the like, can be provided. This contributes to conducting an epidemiological investigation and an investigation into particulate matter emission sources, and to taking measures against air pollution.

Still further, according to the present embodiment, the measurement part 16 further measures the amount of water-soluble organic matter contained in the solution, and outputs the measurement result. The recording part 17 further records the measurement result of the amount of water-soluble organic matter, which is outputted from the measurement part 16. In this manner, the amount of water-soluble organic matter contained in the particulate matter 11 in the atmosphere can be measured.

Still further, according to the present embodiment, the filter 12 is formed in a tape-like shape. The suspended particulate matter measurement apparatus 10 is configured to include the filter feeder 18. The filter feeder 18 continuously feeds the tape-like filter 12. As a result, at least one of the following can be continuously measured for particulate matter 11 in the atmosphere: the amount of nitrate ion contained therein; the amount of sulfate ion contained therein; and the acidity thereof.

Still further, according to the present embodiment, the suction part 13 causes particulate matter 11 in which the mass proportion of particles whose diameter exceeds a predetermined particle diameter is large, and the particulate matter 11 in which the mass proportion of particles whose diameter is equal to or less than the predetermined particle diameter is large, to be collected at different positions on the filter 12, respectively. This enables measurement of components of particulate matter 11 that has such a particle diameter as to have particularly significant effects on the human body. There is a correlation between the particle diameter of particulate matter 11 and the effects of the particulate matter 11 on the human body. Since the suspended particulate matter measurement apparatus 10 is capable of classifying particulate matter 11 with reference to a predetermined particle diameter, the suspended particulate matter measurement apparatus 10 can perform measurement with a focus on, among particulate matter 11 of various particle diameters, particulate matter 11 having such a particle diameter as to have significant effects on the human body, and measure at least one of the following for such particulate matter 11: the amount of nitrate ion contained therein, the amount of sulfate ion contained therein, and the acidity thereof.

Fine particles having a particle diameter of 2.5 µm or less are considered to have particularly harmful effects on the human body. Therefore, being able to classify particulate matter into fine particles and coarse particles and analyze distinctive components of each class of particles, can make a significant contribution to an epidemiological investigation and an investigation into the causes of air pollution.

Still further, according to the present embodiment, the measurement part 16 measures the mass of the particulate matter 11 collected at the filter 12, by using a beta ray absorption method. In this manner, the entire amount of particulate matter 11 contained in a fixed amount of air in the atmosphere can be measured. Also, at least one of the amount of nitrate ion and the amount of sulfate ion contained in a fixed amount of particulate matter 11 can be measured. Accordingly, the proportion of the amount of nitrate ion or sulfate ion in the entire particulate matter 11 can be determined. This contributes to conducting an epidemiological investigation and an investigation into particulate matter emission sources, and to taking measures against air pollution.

In the measurement using a beta ray absorption method, the mass of the particulate matter 11 collected at the filter 12 can be measured without causing chemical alteration of the particulate matter 11. Also, the particulate matter 11 collected at the filter 12 is not consumed in the measurement of the mass. Therefore, the particulate matter 11 collected at the filter 12 can be entirely extracted using a solvent, and a resultant solution containing the components of the particulate matter 11 can be collected. This prevents errors from occurring when measurement different from the mass measurement is performed on the particulate matter 11.

Still further, according to the present embodiment, the measurement part 16 measures the amount of nitrate ion in the solution by using an absorbance method with which to measure absorbances of the solution at predetermined wavelengths. Accordingly, even if the amount of nitrate ion contained in the solution is less than a scale of, for example, several nanomole per cubic meter (several nmol/m$^3$), the amount of nitrate ion can be measured with high precision. Still further, the amount of nitrate ion can be measured within a shorter time period than in a case where, for example, the amount of nitrate ion is measured by ion chromatography. Still further, the amount of nitrate ion contained in the collected particulate matter 11 can be measured within a shorter time period than a time period required for collecting the particulate matter 11. Still further, the measurement apparatus according to the present embodiment can be provided as a more simplified and convenient and less expensive apparatus than an ion chromatograph.

Still further, according to the present embodiment, the measurement part 16 measures the amount of sulfate ion in the solution by barium sulfate turbidimetry. Accordingly, even if the amount of sulfate ion contained in the solution is less than a scale of, for example, several grams, the amount of sulfate ion can be measured with high precision. Still further, the amount of sulfate ion can be measured within a shorter time period than in a case where, for example, the amount of sulfate ion is measured by ion chromatography. Still further, the amount of sulfate ion contained in the collected particulate matter 11 can be measured within a shorter time period than a time period required for collecting the particulate matter 11.

Still further, according to the present embodiment, the measurement part 16 measures the amount of water-soluble organic matter in the solution by an absorbance method with which to measure an absorbance of the solution at a predetermined wavelength. Accordingly, the amount of water-soluble organic matter can be measured within a shorter time period than a time period required for collecting the particulate matter 11. Therefore, even if the collection of particulate matter 11 for the next measurement is performed in parallel with the extraction and measurement of particulate matter 11 that has already been collected, the measurement of the particulate matter 11 collected next can be performed without having to wait for the end of the preceding measurement by the measurement part 16. Since the extraction and measurement of the collected particulate matter 11 can be performed immediately after the collection, the possibility of systematic errors being contained in the measurement result due to a presence of a time period during which the collected particulate matter 11 is left unmeasured until the preceding measurement by the measurement part 16 is completed, can be minimized. Since the collection of particulate matter 11 for the next measurement can be started immediately after the end of the preceding collection of particulate matter 11, the measurement of particulate matter 11 contained in the atmosphere can be continuously performed.

Still further, according to the present embodiment, the measurement part 16 measures the acidity of the solution after a pH indicator being added to the solution, by using an absorbance method with which to measure absorbances of the solution at particular wavelengths. In this manner, the acidity of the solution that contains the particulate matter 11 can be measured by using the measurement part 16 that measures at least one of nitrate ion and sulfate ion. Thus, the measurement apparatus can be simplified as compared to a case where, for example, the acidity is measured by using a pH electrode.

Still further, according to the present embodiment, the amount of nitrate ion in the solution is measured in the nitrate ion measurement process by using an absorbance method with which to measure absorbances of the solution at predetermined wavelengths. In the acidity measurement process performed after the nitrate ion measurement process, a pH indicator is added to the solution, and the acidity of the solution is measured by using an absorbance method with which to measure absorbances of the solution at particular wavelengths. In the sulfate ion measurement process performed after the acidity measurement process, the amount of sulfate ion is measured by barium sulfate turbidimetry.

Accordingly, in the nitrate ion measurement process, the measurement can be performed without adding a reagent to the solution that has been collected at the extraction part 14. Since the pH indicator is added in the acidity measurement process, the measurement can be performed in the acidity measurement process even after the nitrate ion measurement process. Since the added barium chloride and sulfate ion are suspended in the solution in the sulfate ion measurement process, the measurement can be performed in the sulfate ion measurement process even after the acidity measurement process. Thus, at least these three types of measurements can be performed using the same solution. Further, since the nitrate ion measurement process, the acidity measurement process, and the sulfate ion measurement process can use a common UV-Vis spectrophotometer, the measurement apparatus can be simplified as compared to a case where different measurement apparatuses are used in the respective measurement processes.

The suspended particulate matter measurement apparatus 10 is configured to include the filter feeder 18 and the delay part 46. The filter 12 is formed in a tape-like shape from a material having flexibility. The filter feeder 18 continuously feeds the tape-like filter 12. The delay part 46 is located at the position which is farther toward the downstream side of the moving direction X in which the filter 12 is fed, than the collection position 39 where the suction part 13 performs air suction, and which is farther toward the upstream side of the moving direction X, than the position where the extraction of particulate matter 11 is performed with a solvent. Also, the delay part 46 partly delays the movement of the filter 12 along the moving direction X.

Accordingly, at the position where the air suction is performed, classified particulate matter 11 is adhered to different portions of the filter 12. At the collection of the particulate matter 11 from the filter 12, the extraction part 14, which is a single extraction part, can perform the collection a plurality of times, thereby collecting the entire particulate matter 11. Since the collection of the particulate matter 11 can be performed using the single extraction part 14, the measurement apparatus can be simplified as compared to a case where a plurality of extraction parts 14 are provided.

In the present embodiment, the suspended particulate matter measurement apparatus 10 is configured to be able to measure all of the mass, the amount of nitrate ion, the amount of water-soluble organic matter, the amount of sulfate ion, and the acidity. However, in another embodiment, the apparatus may be configured to measure any one or two of the amount of nitrate ion, the amount of sulfate ion, and the acidity, for example.

Second Embodiment

Figure 15:
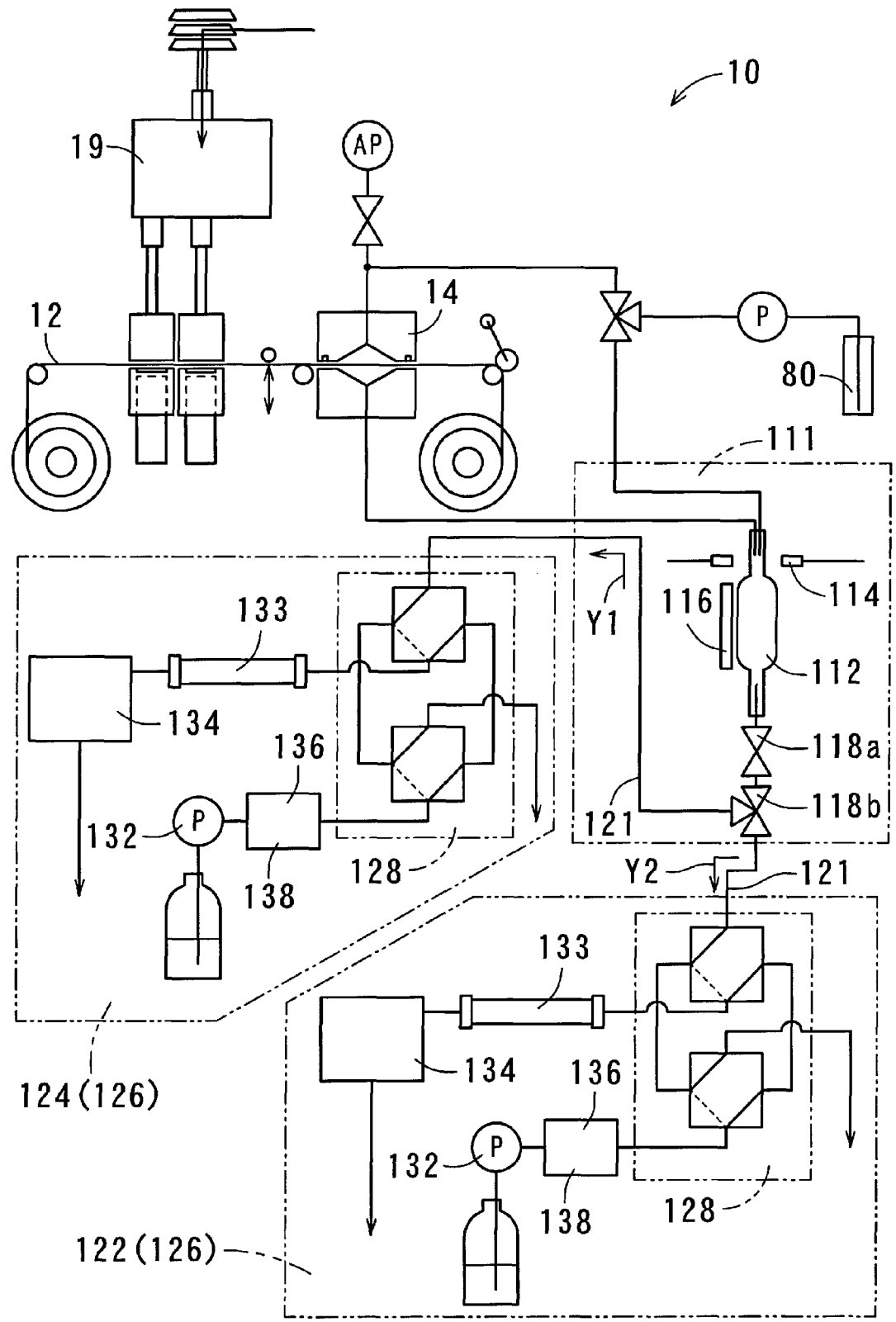
FIG. 15 shows a structure of the suspended particulate matter measurement apparatus 10 according to a second embodiment of the present invention.

FIG. 15 shows a structure of the suspended particulate matter measurement apparatus 10 according to the second embodiment of the present invention. The suspended particulate matter measurement apparatus 10 according to the second embodiment is similar to the suspended particulate matter measurement apparatus 10 according to the first embodiment. Hereinafter, descriptions are given with a focus on the differences between the first embodiment and the second embodiment. The measurement part 16 is capable of performing measurement by either ion chromatography or mass spectrometry. In the second embodiment, the measurement part 16 performs measurement by ion chromatography.

The suspended particulate matter measurement apparatus 10 includes a measuring part 111. The measuring part 111 stores a solution collected by the extraction part 14. The solution collected by the extraction part 14 contains components that have been extracted from particulate matter by dissolving the particulate matter in a solvent. After being collected by the extraction part 14, the solution is conveyed to the measuring part 111 by a pressure produced by an air pump. When the solution has been conveyed to the measuring part 111, a solvent is added to the solution at the measuring part 111, such that the amount of the solution is adjusted to a predetermined solution amount.

The measuring part 111 includes a solution reservoir 112, a level sensor 114, a vibrator 116, and valves 118a and 118b. The solution reservoir 112 retains the solution at the measuring part 111. The level sensor 114 determines whether or not the entire amount of the solution has reached the predetermined solution amount. The vibrator 116 applies vibration to the solution of which the amount has been increased at the measuring part 111, thereby preventing a localized concentration in the solution and assuring a uniform solution concentration.

The valves 118a and 118b are arranged so as to be farther, toward the downstream side of a flow path direction Y2 in which the solution is conveyed from the extraction part 14 to the measuring part 111, than the solution reservoir 112. Formed between the solution reservoir 112 and the measurement part 16 are flow paths 121 for conveying the solution. The valve 118a allows the solution to flow or stops the flow of the solution. The valve 118b controls a direction in which the solution is to flow. The entire amount of the solution stored in the solution reservoir 112 is adjusted to a predetermined solution amount when the valve 118a is in a closed state. Then, the valve 118a is opened and thereby the solution stored in the solution reservoir 112 is conveyed to the measurement part 16. In the second embodiment, the flow path branches at the valve 118b into: a flow path connected to an anion measurement part 124, the flow path extending in a flow path direction Y1; and a flow path connected to a cation measurement part 122, the flow path extending in the flow path direction Y2.

In the second embodiment, the measurement part 16 includes at least one of: the cation measurement part 122 that detects positive ions and performs ion chromatography; and the anion measurement part 124 that detects negative ions and performs ion chromatography. The cation measurement part 122 detects cations, i.e., positive ions, and performs ion chromatography. The anion measurement part 124 detects anions, i.e., negative ions, and performs ion chromatography. A flow path direction in which the solution flows is determined by the valve 118b. The flow path 121 extending in the flow path direction Y1 is connected to the anion measurement part 124, and the flow path 121 extending in the flow path direction Y2 is connected to the cation measurement part 122.

Although materials used as a filler and an eluent are different between the cation measurement part 122 and the anion measurement part 124, these measurement parts are similar to each other in terms of mechanical configuration. When the cation measurement part 122 and the anion measurement part 124 are referred to as ion chromatograph parts that are further simply referred to as "IC parts" (126), each IC part 126 includes a sample loop section 128, a pump section 132, a column 133, and a detector 134. The column 133 is filled with a filler of a type that suits the IC part 126 including the column 133. Through each flow path 121 along which the column 133 is provided, an eluent of a type that suits the corresponding IC part 126 flows at a predetermined flow rate from the upstream side to the downstream side of the flow path direction. Each pump section 132 supplies the eluent from a container that stores the eluent, and applies a driving force to a flow of the eluent. Each pump section 132 is provided with a pump, a damper 136, and an air bubble release valve 138. The damper 136 suppresses variation in a flow rate determined by the pump. The air bubble release valve 138 removes air bubbles contained in the eluent that flows through the flow path 121 from the pump side to the column 133 side.

A cation exchange resin having sulfone groups on the surface may be used as the filler in the cation measurement part 122. Alternatively, in another embodiment, a cation exchange resin formed of a styrene-based gel and having chemically modified carboxyl groups on the surface may be used, for example. In the second embodiment, the eluent used in the cation measurement part 122 is hydrochloric acid of 11 mmol/L. In another embodiment, a sulfuric acid aqueous solution of 11 mmol/L or a methanesulfonic acid aqueous solution of 20 mmol/L may be used, for example. In another further embodiment, an aqueous solution in which the concentration of nitric acid is 2.5 mmol/L and the concentration of histidine is 0.5 mmol/L may be used. The filler and eluent used in the cation measurement part 122 are not limited to the above filler and eluent.

A hydrophilic polymer gel having chemically modified quaternary ammonium on the surface may be used as the filler in the anion measurement part 124. The eluent used in the anion measurement part 124 may be an aqueous solution in which the concentration of p-hydroxybenzoic acid is 8.0 mmol/L, the concentration of Bis-Tris is 3.2 mmol/L, and the concentration of boric acid is 50 mmol/L. Bis-Tris is an abbreviation for bis(2-hydroxyethyl)iminotris(hydroxymethyl)-methane. The filler and eluent used in the anion measurement part 124 are not limited to the above filler and the eluent.

Each sample loop section 128 is disposed so as to be farther toward the upstream side of the corresponding flow path direction than the column 133. Each sample loop section 128 guides the solution from the measuring part 111 to the column 133. The solution of which the amount has been adjusted at the measuring part 111 is, when being introduced into each IC part, conveyed to the sample loop section 128 of each IC part, and a fixed amount of the solution is stored at the sample loop section 128. The remaining surplus solution is discarded. Thereafter, at the feeding of the solution into the column 133, the eluent in the pump section 132 is conveyed to the sample loop section 128, and the solution stored in the sample loop section 128 is forced into the column 133. The detector 134 detects presence of solutes based on changes in electric conductivity of the solution. In another embodiment, the detector 134 may detect presence of solutes by measuring changes in refractive index of the solution. The solution having passed through the detector 134 is discarded.

At each IC part 126, time points at which different positive or negative ions pass through the detector 134 are different from each other since these ions pass through the column 133. Predetermined positive ions and negative ions may be fed into the IC parts 126, and time periods elapsed from when the feeding has been performed until the respective ions are detected by the detectors 134 may be measured in advance. By comparing these data with data that are obtained when the solution containing the extracted particulate matter is measured, positive ions and negative ions detected by the detectors 134 of the IC parts 126 can be identified.

Further, various positive and negative ions of predetermined concentrations are fed into the IC parts 126, and the magnitudes of emergence peaks of the ions, which are detected by the detectors 134, are measured, whereby a relationship between the peak area of the emergence peak of each ion and the concentration thereof is determined. By comparing these data with data that are obtained when the solution containing the extracted particulate matter is measured, the concentrations of positive ions and negative ions detected by the detectors 134 of the IC parts 126 can be specified. The feeding of the solution to the IC parts 126 is automatically and intermittently performed. Also, measurement by the detectors 134 of the IC parts 126, data outputs from the detectors 134, and data recording by the recording part are also automatically performed in accordance with the timing of the feeding. In each IC part 126, the flow rate of the solution containing the eluent is 0.5 ml/min. However, the flow rate is not limited thereto. If the emergence peaks of the ions have similar shapes to each other, then measurement results can be obtained on the assumption that the concentration of each ion corresponds to the height of the emergence peak thereof.

Figure 16:
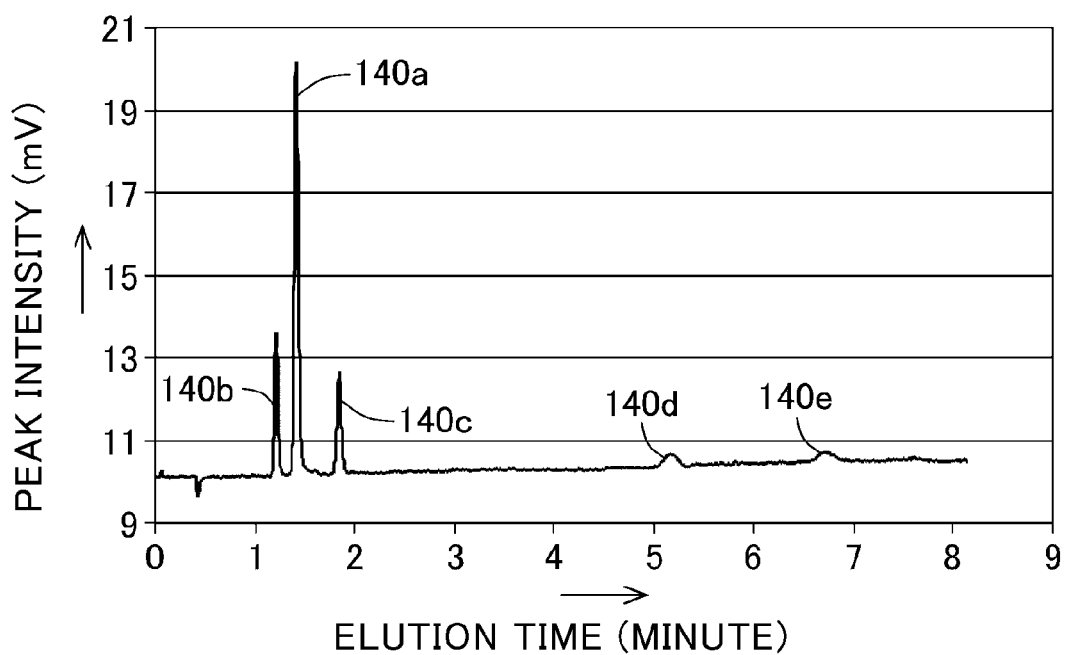
FIG. 16 shows an example of measurement results obtained by a cation measurement part 122 of the second embodiment of the present invention.

FIG. 16 shows an example of measurement results obtained by the cation measurement part 122 of the second embodiment of the present invention. In FIG. 16, the vertical axis indicates the amounts of changes in electric conductivity of the solution, which are obtained corresponding to the concentrations of various positive ions in the solution, the vertical axis indicating the amounts of changes as emergence peaks of these various positive ions. The horizontal axis indicates elution time. The elution time is measured from a time point at which the solution arrives at the cation measurement part 122. However, in another embodiment, the elution time may be measured from a time point at which a particular type of solute whose elution time in a cation column is sufficiently long has been eluted.

In FIG. 16, a first peak 140a that is the greatest peak appearing corresponding to an elution time of 1.3 to 1.5 minutes represents an emergence peak of ammonium ion ($NH_4^+$); a second peak 140b appearing at approximately 1.2 minutes represents an emergence peak of sodium ion ($Na^+$); a third peak 140c appearing at approximately 1.8 to 1.9 minutes represents an emergence peak of potassium ion ($K^+$); a fourth peak 140d appearing at approximately 5.1 minutes represents an emergence peak of magnesium ion ($Mg^+$); and a fifth peak 140e appearing at approximately 6.8 minutes represents an emergence peak of calcium ion ($Ca^+$).

In the calculation of the concentrations of the respective ions, measurement is first performed on a plurality of types of standard samples of known concentrations under the same conditions. Then, a relationship between each peak area of emergence peaks obtained as a result of the measurement and a corresponding concentration is obtained as a calibration curve. Next, when emergence peaks of the respective ions are obtained as a result of actual target measurement, concentrations corresponding to the peak areas of these emergence peaks are each determined based on the calibration curve. Based on the measurement results shown in FIG. 16, the concentrations of the respective positive ions contained in the atmosphere are determined as follows: the concentration of $Na^+$ is 6.09 $nmol/m^3$; the concentration of $NH_4^+$ is 73.4 $nmol/m^3$; and the concentration of $K^+$ is 8.36 $nmol/m^3$.

Figure 17:
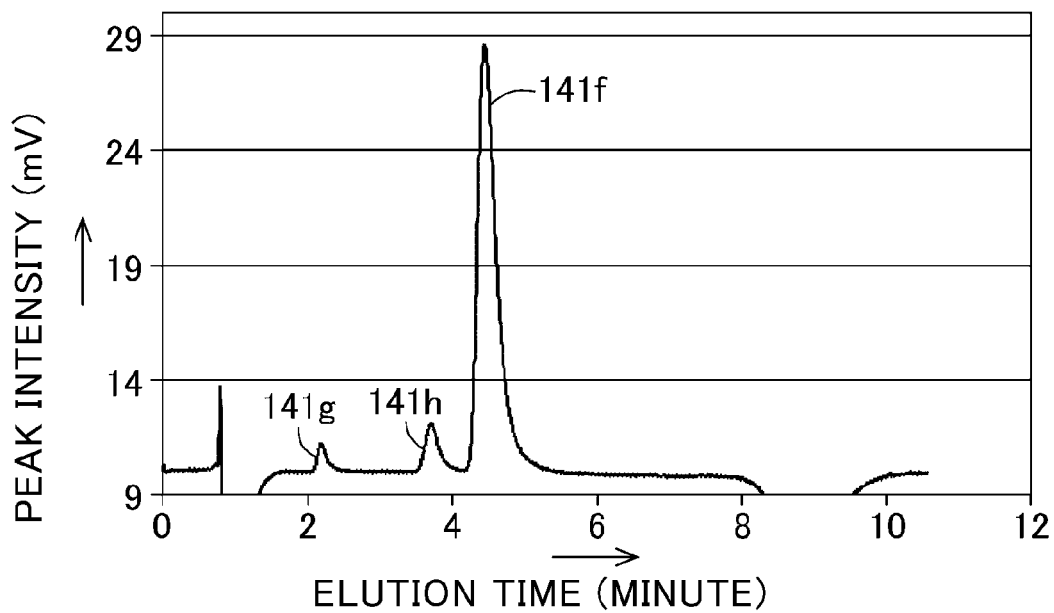
FIG. 17 shows an example of measurement results obtained by an anion measurement part 124 of the second embodiment of the present invention.

FIG. 17 shows an example of measurement results obtained by the anion measurement part 124 of the second embodiment of the present invention. In FIG. 17, the vertical axis indicates the amounts of changes in electric conductivity of the solution, which are obtained corresponding to the concentrations of various negative ions in the solution, the vertical axis indicating the amounts of changes as emergence peaks of these various negative ions. The horizontal axis indicates elution time. The elution time is measured from a time point at which the solution arrives at the anion measurement part 124. However, in another embodiment, the elution time may be measured from a time point at which a particular type of solute whose elution time in an anion column is sufficiently long has been eluted.

In FIG. 17, a sixth peak 141f that is the greatest peak appearing corresponding to an elution time of approximately 4.5 minutes represents an emergence peak of sulfate ion ($SO_4^{2-}$); a seventh peak 141g appearing at approximately 2.2 minutes represents an emergence peak of chloride ion (CL); and an eighth peak 141h appearing approximately at 3.7 minutes represents an emergence peak of nitrate ion ($NO_3^-$). Similarly to the manner of determining the concentrations of positive ions, in the case of determining the concentrations of negative ions, a correspondence relationship between the peak area of an emergence peak of each ion and the concentration thereof is obtained as a calibration curve. By using the calibration curve obtained for each ion, the concentration of each ion is determined based on the peak area of an emergence peak obtained for said each ion. Based on the measurement results shown in FIG. 17, the concentration of each negative ion contained in the atmosphere is determined as follows: the concentration of $Cl^-$ is 5.43 $nmol/m^3$, the concentration of $NO_3^-$ is 53.4 $nmol/m^3$; and the concentration $SO_4^{2-}$ is 312 $nmol/m^3$.

According to the second embodiment, the measurement part 16 performs measurement by ion chromatography. Therefore, unlike other types of chromatography, molecules are not adsorbed onto the columns or samples to be measured are not required to have high volatility, for example. Accordingly, the measurement part 16 of the second embodiment is able to measure, for example, $SO_4^-$, $NO_3^-$, $Cl^-$, $F^-$, $Na^+$, $NH_4^+$, $K^-$, $Mg^+$, and $Ca^-$ that are contained in the particulate matter 11.

Third Embodiment

Figure 18:
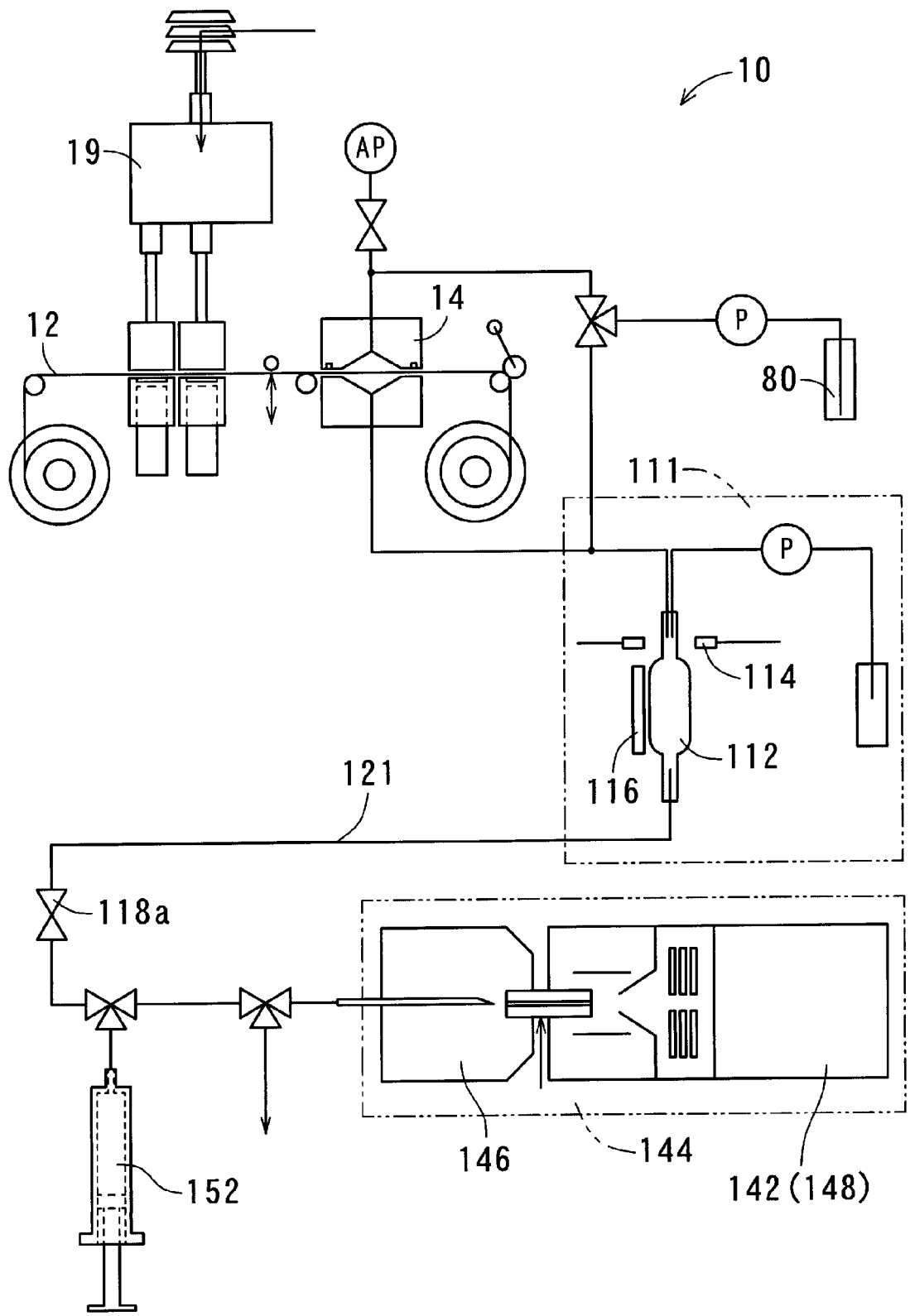
FIG. 18 shows a structure of the suspended particulate matter measurement apparatus 10 according to a third embodiment of the present invention.

FIG. 18 shows a structure of the suspended particulate matter measurement apparatus 10 according to the third embodiment of the present invention. The suspended particulate matter measurement apparatus 10 according to the third embodiment is similar to the suspended particulate matter measurement apparatus 10 according to the second embodiment. Hereinafter, descriptions are given with a focus on the differences between the second embodiment and the third embodiment. The measurement part 16 performs measurement by either ion chromatography or mass spectrometry. In the third embodiment, the measurement part 16 performs measurement by mass spectrometry, and includes a quadrupole mass analyzer 142. The measurement part 16 uses electrospray ionization to perform ionization in mass spectrometry.

Hereinafter, a measurement apparatus performing mass spectrometry is referred to as a "mass spectrometer" (144). The mass spectrometer 144 includes an ionization section 146 and an analysis section 148. The ionization section 146 applies an electric charge to molecules contained in a solution conveyed to the mass spectrometer 144, thereby ionizing the molecules. The analysis section 148 measures the mass of the ionized molecules. In the third embodiment, the ionization section 146 uses electrospray ionization (abbreviated as "ESI") to ionize the molecules.

The ESI method allows the energy applied to the molecules to be lower than other various ionization methods such as fast atom bombardment (abbreviated as "FAB") and electron ionization (abbreviated as "EI"). Therefore, there is less chance of a chemical bond between molecules being broken, and molecular fragmentation can be suppressed, accordingly. The mass spectrometer 144 using the ESI method may be referred to as "ESI-MS".

The analysis section 148 is realized by the quadrupole mass analyzer 142, and performs mass spectrometry using a quadrupole. An alternating electric field of high frequency is formed among four rod members with which the quadrupole is realized. Molecules of a specific molecular weight are detected based on setting of the frequency. The molecular weight of molecules to be detected is varied through frequency sweep, and thereby molecules of various molecular weights are detected. In this manner, molecules contained in the sample conveyed to the analysis section 148 are detected for each molecular weight. The mass spectrometer using the quadrupole mass analyzer 142 may be referred to as a "Q-MS". When quadrupole mass spectrometry using the four rod members is performed, a space through which the molecules in the sample pass is not required to be in a high vacuum condition. However, generally speaking, sensitivity is increased if the space is in a high vacuum condition. Using a quadrupole mass analyzer is more advantageous to measure a substance of which the mass-to-charge value is small, than using a time of flight (abbreviated as "TOF") mass spectrometer.

In the third embodiment, the flow path 121 that is formed so as to extend from the measuring part 111 toward the downstream side of a flow path direction, is connected to the measurement part 16 as a single flow path 121 without being branched. The solution conveyed from the measuring part 111 toward the downstream side of the flow path 121 is temporarily stored in a syringe 152, and then injected from the syringe 152 into the ionization section 146 at a predetermined flow rate. The injection of the solution by the syringe 152 into the mass spectrometer 144 is automatically and intermittently performed. Measurement and data outputs by the mass spectrometer 144, and data recording by the recording part are also automatically performed in accordance with the timing of the injection by the syringe 152. In the third embodiment, the ionization section 146 is an ESI-MS. However, in another embodiment, the ionization may be performed by atmospheric pressure photoionization (abbreviated as "APPI"). In the third embodiment, the flow rate at which the solution injected by the syringe flows is 10 μl/min.

When the measurement by the ionization section 146 and the analysis section 148 is not performed, the solution to be conveyed from the syringe 152 to the ionization section 146 is discarded at a position located along the flow path 121, without being injected into the ionization section 146. Also, the solution having passed through the analysis section 148 is discarded.

FIG. 19 shows an example of measurement results obtained by the mass spectrometer 144 according to the third embodiment of the present invention. A mixed solvent in which water and acetonitrile in the same volume as the water are mixed in the volume ratio of 1:1, is used for the solution that flows through the flow path 121 and that is to be injected into the mass spectrometer 144. In FIG. 19, the greatest peak, of which the mass per charge (hereinafter, "m(mass)/z (charge)") is 96.6, is the peak of sulfate ion ($HSO_4^-$). In FIG. 19, the second greatest peak of which m/z is 166.7 can be regarded as the peak of ion of water-soluble organic matter whose molecule is hereinafter provisionally referred to as "M".

In FIG. 19, the third greatest peak of which m/z is 229.8 is the peak of "$M+NO_3$" that is a result of nitrate ion being attached to the molecule M of the water-soluble organic matter. In FIG. 19, the fourth greatest peak of which m/z is 334.9 is the peak of a dimmer of the molecule M of the water-soluble organic matter. In FIG. 19, the fifth greatest peak of which m/z is 264.8 is the peak of "$M+HSO_4$" that is a result of sulfate ion being attached to the molecule M of the water-soluble organic matter. Further, in FIG. 19, other peaks such as the peaks of nitrate ion ($NO_3$), ion of sodium sulfate ($NaSO_4^-$), and oxalic acid ion ($HOOC-COO^-$) are confirmed.

According to the second and third embodiments, the measurement part 16 performs measurement by either ion chromatography or mass spectrometry. In this manner, electrically charged substances and easily electrified substances that are contained in suspended particulate matter can be measured. Easily ionized substances are often associated with the acidity of suspended particulate matter. Therefore, by measuring such substances, information that contributes to identifying substances associated with the acidity can be obtained.

According to the third embodiment, the measurement part 16 performs measurement by mass spectrometry, and includes the quadrupole mass analyzer 142. As a result, the collection and measurement of suspended particulate matter can be completed within a shorter time period than the collection and measurement that involve manual work. For example, the measurement by the mass spectrometer 144 including the quadrupole mass analyzer 142 is completed in approximately 10 minutes after the start of the measurement. Accordingly, it is of course possible to continuously perform both the collection and the measurement 24 times a day, that is, once an hour. Since the measurement can be completed within a short time period, even if the collection of particulate matter for the next measurement is performed in parallel with the measurement of particulate matter that has already been collected and extracted, the measurement of the particulate matter extracted next can be performed without having to wait for the end of the preceding measurement by the measurement part 16. Measurement for obtaining significant data can be completed in approximately ten minutes.

Since the extraction and measurement of the collected particulate matter can be performed immediately after the collection, the possibility of systematic errors being contained in the measurement results due to a presence of a time period during which the collected particulate matter is left unmeasured until the preceding measurement by the measurement part 16 is completed, can be minimized. Since the collection of particulate matter for the next measurement can be started immediately after the end of the preceding collection of particulate matter, the measurement of particulate matter contained in the atmosphere can be continuously performed. Since the mass spectrometer 144 includes the quadrupole mass analyzer 142, the mass spectrometer 144 can be realized as a smaller apparatus than, for example, a TOF mass spectrometer.

Further, according to the third embodiment, the ionization method in mass spectrometry is the ESI method. As a result, ionization can be performed under less severe conditions as compared to a case where a different ionization method, for example FAB or EI, is used. Accordingly, molecular fragmentation can be prevented. This allows a parent peak to be readily specified.

Still further, according to the third embodiment, $HSO_4^-$, $NO_3^-$, $Cl^-$, $Na^+$, $NH_4^+$, $K^+$, $Mg^+$, and $Ca^+$ can be measured. Moreover, in the case where water-soluble organic matter that is easily ionized into positively or negatively charged ions is contained in the solution, such organic matter can also be measured. Of course, the mass spectrometer 144 is capable of measuring the molecular weight of both positively charged molecules and negatively charged molecules.

The extraction part 14, the solution reservoir 112, the valves 118, the flow paths 121, the syringe 152, and the like used in the first to third embodiments, which contact a sample solution, are cleansed with a solvent after the measurement is completed. For example, in the case where the measurement is performed, every hour, after the collection by one-hour continuous air suction is performed, cleansing of the parts that contact the sample solution is performed each time the hourly measurement ends. In the case where the concentration of particulate matter contained in the atmosphere is low, a time period during which the collection is performed by the continuous air suction may be prolonged such that more particulate matter is concentrated onto the filter. In this manner, the measurement can be performed even if the concentration of the particulate matter is low. In the third embodiment, the mass spectrometer 144 is disposed so as to be farther toward the downstream side of the flow path direction Y2 than the measuring part 111. In another embodiment, for example, the flow path 121 may be branched similarly to the second embodiment, and one or two IC parts 126 and the mass spectrometer 144 may be arranged so as to be farther toward the downstream side of the flow path direction Y2 than the measuring part 111.

While the invention has been described in detail, the foregoing description is in all aspects illustrative and not restrictive. It is understood that numerous other modifications and variations can be devised without departing from the scope of the invention.

What is claimed is:

1. An atmospheric nitrate-ion measurement method comprising:
   a collection step of suctioning atmospheric air at a constant flow rate of at least 90 liters per hour through a filter to collect particulate matter from the suctioned air on the filter;
   an extraction step of
   i. contacting the filter with a solvent, of relative volume that is less than or equal to $1.1 \times 10^{-5}$ times the volume of air suctioned per hour by the suction part, to extract the particulate matter on the filter and dissolve the particulate matter into the solvent,
   ii. collecting the resultant solution, and
   iii. feeding the solution from said extraction step into a measuring means;
   a nitrate-ion measurement step of measuring the optical absorbance of the solution with the measuring means at predetermined wavelengths, to obtain characteristic absorbance spectra correlating to amount of nitrate ions in the solution; and
   a recording step of recording the measurement results obtained in said nitrate-ion measurement step.

2. An atmospheric sulfate-ion measurement method comprising:
   a collection step of suctioning atmospheric air at a constant flow rate of at least 90 liters per hour through a filter to collect particulate matter from the suctioned air on the filter;
   an extraction step of
   i. contacting the filter with a solvent, of relative volume that is less than or equal to $1.1 \times 10^{-5}$ times the volume of air suctioned per hour by the suction part, to extract the particulate matter on the filter and dissolve the particulate matter into the solvent,
   ii. collecting the resultant solution, and
   iii. feeding the solution from said extraction step into a measuring means;
   a sulfate-ion measurement step of measuring the transmitted light intensity of the solution by barium-sulfate turbidimetry with the measuring means to obtain characteristic spectra of transmitted light intensities correlating to amount of sulfate ions in the solution; and
   a recording step of recording the measurement results obtained in said sulfate-ion measurement step.

3. An atmospheric acidity measurement method comprising:
   a collection step of suctioning atmospheric air at a constant flow rate of at least 90 liters per hour through a filter to collect particulate matter from the suctioned air on the filter;
   an extraction step of
   i. contacting the filter with a solvent, of relative volume that is less than or equal to $1.1 \times 10^{-5}$ times the volume of air suctioned per hour by the suction part, to extract the particulate matter on the filter and dissolve the particulate matter into the solvent,
   ii. collecting the resultant solution, and
   iii. feeding the solution from said extraction step into a measuring means;
   an acidity measurement step of determining the acidity of the particulate matter in the solution by adding a pH indicator to the solution and measuring its optical absorbance with the measuring means at predetermined wavelengths; and
   a recording step of recording the measurement results obtained in said acidity measurement step.

4. An atmospheric water-soluble organic matter measurement method comprising:
   a collection step of suctioning atmospheric air at a constant flow rate of at least 90 liters per hour through a filter to collect particulate matter from the suctioned air on the filter;
   an extraction step of
   i. contacting the filter with a solvent, of relative volume that is less than or equal to $1.1 \times 10^{-5}$ times the volume of air suctioned per hour by the suction part, to extract the particulate matter on the filter and dissolve the particulate matter into the solvent,
   ii. collecting the resultant solution, and
   iii. feeding the solution from said extraction step into a measuring means;
   a water-soluble organic matter measurement step of measuring the optical absorbance of the solution with the measuring means at a predetermined wavelength to measure the amount of water-soluble organic matter in the solution; and
   a recording step of recording the measurement results obtained in said water-soluble organic matter measurement step.

5. A method according to any one of claims 1 through 4, wherein in said measurement step, the measuring means is either ion chromatography or mass spectrometry.

6. A method according to claim 5, wherein in said measurement step, the measuring means is mass spectrometry employing a quadrupole mass spectrometer.

7. A method according to claim 6, wherein in said measurement step, electrospray ionization is employed to ionize easily ionized substances that are contained in the particulate matter in the solution.

8. A method according to claim 5, wherein in said measurement step, the measuring means is ion chromatography employing one of either cation exchange chromatography for detecting positive ions or anion exchange chromatography for detecting negative ions.

9. A method according to any one of claims 1 through 4, wherein in said collection step the atmospheric air is suctioned through a classifier separating the air into at least a first flow containing suspended particulate matter greater than a predetermined size and a second flow containing suspended particulates less than or equal to the predetermined size, and the first and second flows are passed through respective areas of the filter to collect particulates from the suctioned air on the respective areas of the filter.

10. A method according to any one of claims 1 through 4, further including a substep, prior to said extraction step, of measuring, by beta-ray absorption, the mass of the particulate matter collected on the filter.

11. An atmospheric nitrate-ion, acidity, and sulfate-ion measurement method comprising:

a collection step of suctioning atmospheric air at a constant flow rate of at least 90 liters per hour through a filter to collect particulate matter from the suctioned air on the filter;

an extraction step of
  i. contacting the filter with a solvent, of relative volume that is less than or equal to $1.1 \times 10^{-5}$ times the volume of air suctioned per hour by the suction part, to extract the particulate matter on the filter and dissolve the particulate matter into the solvent,
  ii. collecting the resultant solution, and
  iii. feeding the solution from said extraction step into a measuring means;

a nitrate-ion measurement step of measuring the optical absorbance of the solution with the measuring means at predetermined wavelengths, to obtain characteristic absorbance spectra correlating to amount of nitrate ions in the solution;

an acidity measurement step, after said nitrate-ion measurement step, of determining the acidity of the particulate matter in the solution by adding a pH indicator to the solution and measuring its optical absorbance with the measuring means at predetermined wavelengths;

a sulfate-ion measurement step, after said acidity measurement step, of measuring the transmitted light intensity of the solution by barium-sulfate turbidimetry with the measuring means to obtain characteristic spectra of transmitted light intensities correlating to amount of sulfate ions in the solution; and a recording step of recording the measurement results obtained in said nitrate-ion, acidity, and sulfate-ion measurement steps.

12. An atmospheric nitrate-ion, acidity, and sulfate-ion measurement method according to claim 11, wherein in said nitrate-ion measurement step the amount of water-soluble organic matter in the solution is also measured, by an absorbance technique at a predetermined wavelength at which nitrate ions do not exhibit absorption, to refine the nitrate-ion measurement.

13. An atmospheric nitrate-ion, acidity, and sulfate-ion measurement method according to claim 11, further including, prior to said extraction step:

a substep of measuring, by beta-ray absorption, the mass of the particulate matter collected on the respective areas of the filter; and a substep of measuring the amount of optical black carbon in the particulate matter collected on the area of the filter corresponding to the second flow.

* * * * *